(12) United States Patent
Stasko et al.

(10) Patent No.: US 9,526,738 B2
(45) Date of Patent: Dec. 27, 2016

(54) TOPICAL GELS AND METHODS OF USING THE SAME

(75) Inventors: Nathan Stasko, Durham, NC (US); Susanne Bauman, Durham, NC (US); Pranav R. Joshi, Karnataka (IN)

(73) Assignee: Novan, Inc., Durham, NC (US)

( * ) Notice: Subject to any disclaimer, the term of this patent is extended or adjusted under 35 U.S.C. 154(b) by 379 days.

(21) Appl. No.: 13/256,928

(22) PCT Filed: Aug. 20, 2010

(86) PCT No.: PCT/US2010/046173
§ 371 (c)(1),
(2), (4) Date: Oct. 4, 2011

(87) PCT Pub. No.: WO2011/022652
PCT Pub. Date: Feb. 24, 2011

(65) Prior Publication Data
US 2012/0134951 A1    May 31, 2012

Related U.S. Application Data

(60) Provisional application No. 61/235,933, filed on Aug. 21, 2009.

(51) Int. Cl.
| | | |
|---|---|---|
| A61K 9/14 | (2006.01) | |
| A61K 31/655 | (2006.01) | |
| A61K 9/00 | (2006.01) | |
| A61K 9/06 | (2006.01) | |
| A61K 33/00 | (2006.01) | |
| A61K 47/24 | (2006.01) | |
| A61K 47/48 | (2006.01) | |

(52) U.S. Cl.
CPC ........... *A61K 31/655* (2013.01); *A61K 9/0014* (2013.01); *A61K 9/06* (2013.01); *A61K 33/00* (2013.01); *A61K 47/24* (2013.01); *A61K 47/48192* (2013.01); *A61K 47/48784* (2013.01)

(58) Field of Classification Search
CPC ........... A61K 8/72; A61K 8/89; A61K 8/891; A61K 8/73; A61K 8/732; A61K 9/0012; A61K 9/0014
USPC ........................ 424/401, 402, 77.2, 484–486
See application file for complete search history.

(56) References Cited

U.S. PATENT DOCUMENTS

| | | |
|---|---|---|
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,600,001 A | 7/1986 | Gilman |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 4,985,023 A | 1/1991 | Blank et al. |
| 4,990,338 A | 2/1991 | Blank et al. |
| 5,035,892 A | 7/1991 | Blank et al. |
| 5,045,322 A | 9/1991 | Blank et al. |
| 5,061,487 A | 10/1991 | Blank et al. |
| 5,079,004 A | 1/1992 | Blank et al. |
| 5,380,758 A | 1/1995 | Stamler et al. |
| 5,405,919 A | 4/1995 | Keefer et al. |
| 5,418,301 A | 5/1995 | Hult et al. |
| 5,428,070 A | 6/1995 | Cooke et al. |
| 5,504,117 A | 4/1996 | Gorfine |
| 5,519,020 A | 5/1996 | Smith et al. |
| 5,525,357 A | 6/1996 | Keefer et al. |
| 5,574,068 A | 11/1996 | Stamler et al. |
| 5,593,876 A | 1/1997 | Stamler et al. |
| 5,599,984 A | 2/1997 | Bianchi et al. |
| 5,629,322 A | 5/1997 | Guthikonda et al. |
| 5,632,981 A | 5/1997 | Saavedra et al. |
| 5,650,442 A | 7/1997 | Mitchell et al. |
| 5,650,447 A | 7/1997 | Keefer et al. |
| 5,665,077 A | 9/1997 | Rosen et al. |
| 5,676,963 A | 10/1997 | Keefer et al. |
| 5,691,423 A | 11/1997 | Smith et al. |
| 5,693,676 A | 12/1997 | Gorfine |
| 5,700,830 A | 12/1997 | Korthuis et al. |
| 5,718,892 A | 2/1998 | Keefer et al. |
| 5,726,156 A | 3/1998 | Girten et al. |
| 5,750,573 A | 5/1998 | Bianchi et al. |
| 5,753,684 A | 5/1998 | Bianchi et al. |
| 5,760,001 A | 6/1998 | Girten et al. |

(Continued)

FOREIGN PATENT DOCUMENTS

| | | |
|---|---|---|
| CN | 1387542 | 12/2002 |
| CN | 1612804 | 5/2005 |
| CN | 1819848 | 8/2006 |
| CN | 101189032 | 5/2008 |
| CN | 101242815 | 8/2008 |
| CN | 101287505 | 10/2008 |
| EP | 0 805 678 B1 | 10/2003 |

(Continued)

OTHER PUBLICATIONS

Octanol-Water Partition Coefficients of Simple Organic Compounds, James Sangster, 1988.*
Notification of Transmittal of the International Search Report and the Written Opinion of the International Searching Authority, or the Declaration corresponding to PCT/US2012/45384 mailed Nov. 5, 2012.
Barraud, N., et al., "Involvement of Nitric Oxide in Biofilm Dispersal of Pseudomonas aeruginosa," *Journal of Bacteriology*, 2006, vol. 188(21), pp. 7344-7353.

(Continued)

*Primary Examiner* — Micah-Paul Young
(74) *Attorney, Agent, or Firm* — Myers Bigel, P.A.

(57) ABSTRACT

Provided according to some embodiments of the invention are topical gels that may release nitric oxide. Also provided are methods of using such topical gels in the treatment of wounds and other skin ailments. The topical gels comprise diazeniutndiolate-functionalized polysiloxane macromolecules.

31 Claims, 12 Drawing Sheets

(56) References Cited

U.S. PATENT DOCUMENTS

| | | | |
|---|---|---|---|
| 5,770,645 A | 6/1998 | Stamler et al. |
| 5,786,332 A | 7/1998 | Girten et al. |
| 5,789,447 A | 8/1998 | Wink, Jr. et al. |
| 5,797,887 A | 8/1998 | Rosen et al. |
| 5,810,010 A | 9/1998 | Anbar |
| 5,814,666 A | 9/1998 | Green et al. |
| 5,814,667 A | 9/1998 | Mitchell et al. |
| 5,821,261 A | 10/1998 | Durette et al. |
| 5,837,736 A | 11/1998 | Mitchell et al. |
| 5,840,759 A | 11/1998 | Mitchell et al. |
| 5,849,794 A | 12/1998 | Bianchi et al. |
| 5,852,058 A | 12/1998 | Cooke et al. |
| 5,854,289 A | 12/1998 | Bianchi et al. |
| 5,859,062 A | 1/1999 | Bianchi et al. |
| 5,861,168 A | 1/1999 | Cooke et al. |
| 5,863,890 A | 1/1999 | Stamler et al. |
| 5,891,459 A | 4/1999 | Cooke et al. |
| 5,891,472 A | 4/1999 | Russell |
| 5,910,316 A | 6/1999 | Keefer et al. |
| 5,932,538 A | 8/1999 | Garvey et al. |
| 5,958,427 A | 9/1999 | Salzman et al. |
| 5,961,466 A | 10/1999 | Anbar |
| 5,962,520 A | 10/1999 | Smith et al. |
| 5,968,528 A * | 10/1999 | Deckner et al. ............ 424/401 |
| 5,994,294 A | 11/1999 | Garvey et al. |
| 5,994,444 A | 11/1999 | Trescony et al. |
| 5,999,843 A | 12/1999 | Anbar |
| 6,008,255 A | 12/1999 | Bianchi et al. |
| 6,022,900 A | 2/2000 | Bianchi et al. |
| 6,035,225 A | 3/2000 | Anbar |
| 6,043,358 A | 3/2000 | Caldwell et al. |
| 6,045,827 A | 4/2000 | Russell |
| 6,070,928 A | 6/2000 | Campbell |
| 6,087,479 A | 7/2000 | Stamler et al. |
| 6,103,266 A * | 8/2000 | Tapolsky et al. ............ 424/484 |
| 6,103,275 A | 8/2000 | Seitz et al. |
| 6,110,453 A | 8/2000 | Keefer et al. |
| 6,143,037 A | 11/2000 | Goldstein et al. |
| 6,147,068 A | 11/2000 | Smith et al. |
| 6,151,522 A | 11/2000 | Alfano et al. |
| 6,160,021 A | 12/2000 | Lerner et al. |
| 6,171,232 B1 | 1/2001 | Papandreou et al. |
| 6,174,539 B1 | 1/2001 | Stamler et al. |
| 6,180,082 B1 | 1/2001 | Woltering et al. |
| 6,180,676 B1 | 1/2001 | Bianchi et al. |
| 6,190,704 B1 | 2/2001 | Murrell |
| 6,200,558 B1 | 3/2001 | Saavedra et al. |
| 6,207,855 B1 | 3/2001 | Toone et al. |
| 6,218,016 B1 | 4/2001 | Tedeschi et al. |
| 6,232,336 B1 | 5/2001 | Hrabie et al. |
| 6,232,434 B1 | 5/2001 | Stamler et al. |
| 6,238,683 B1 | 5/2001 | Burnett et al. |
| 6,248,787 B1 | 6/2001 | Bianchi et al. |
| 6,255,277 B1 | 7/2001 | Stamler et al. |
| 6,261,594 B1 | 7/2001 | Smith et al. |
| 6,270,779 B1 | 8/2001 | Fitzhugh et al. |
| 6,287,601 B1 | 9/2001 | Russell |
| 6,290,981 B1 | 9/2001 | Keefer et al. |
| 6,291,424 B1 | 9/2001 | Stamler et al. |
| 6,294,517 B1 | 9/2001 | Garvey et al. |
| 6,299,980 B1 | 10/2001 | Shah et al. |
| 6,323,211 B1 | 11/2001 | Garvey et al. |
| 6,350,467 B1 | 2/2002 | Demopoulos et al. |
| 6,352,709 B1 | 3/2002 | Stamler et al. |
| 6,358,536 B1 | 3/2002 | Thomas |
| 6,359,167 B2 | 3/2002 | Toone et al. |
| 6,359,182 B1 | 3/2002 | Stamler et al. |
| 6,369,071 B1 | 4/2002 | Haj-Yehia |
| 6,372,733 B1 | 4/2002 | Caldwell et al. |
| 6,377,321 B1 | 4/2002 | Khan et al. |
| 6,379,660 B1 | 4/2002 | Saavedra et al. |
| 6,379,691 B1 | 4/2002 | Tedeschi et al. |
| 6,391,895 B1 | 5/2002 | Towart et al. |
| 6,403,759 B2 | 6/2002 | Stamler et al. |
| 6,410,622 B1 | 6/2002 | Endres |
| 6,417,162 B1 | 7/2002 | Garvey et al. |
| 6,432,077 B1 | 8/2002 | Stenzler |
| 6,433,182 B1 | 8/2002 | Garvey et al. |
| 6,436,975 B1 | 8/2002 | Del Soldato |
| 6,441,254 B1 | 8/2002 | Dobert |
| 6,448,267 B1 | 9/2002 | Anggard et al. |
| 6,451,337 B1 | 9/2002 | Smith et al. |
| 6,455,542 B1 | 9/2002 | Anggard et al. |
| 6,469,065 B1 | 10/2002 | Garvey et al. |
| 6,471,978 B1 | 10/2002 | Stamler et al. |
| 6,472,390 B1 | 10/2002 | Stamler et al. |
| 6,474,508 B1 | 11/2002 | Marsh |
| 6,488,951 B2 | 12/2002 | Toone et al. |
| 6,492,405 B2 | 12/2002 | Haj-Yehia |
| 6,511,991 B2 | 1/2003 | Hrabie et al. |
| 6,514,934 B1 | 2/2003 | Garvey et al. |
| 6,538,033 B2 | 3/2003 | Bing |
| 6,560,478 B1 | 5/2003 | Alfano et al. |
| 6,562,344 B1 | 5/2003 | Stamler et al. |
| 6,562,785 B1 | 5/2003 | Shapiro |
| 6,583,113 B2 | 6/2003 | Stamler et al. |
| 6,583,311 B2 | 6/2003 | Toone et al. |
| 6,605,447 B2 | 8/2003 | Weiss et al. |
| 6,610,660 B1 | 8/2003 | Saavedra et al. |
| 6,627,602 B2 | 9/2003 | Stamler et al. |
| 6,642,208 B2 | 11/2003 | Cooke et al. |
| 6,642,260 B2 | 11/2003 | Haj-Yehia |
| 6,645,518 B2 | 11/2003 | Tedeschi et al. |
| 6,646,006 B2 | 11/2003 | Cooke et al. |
| 6,656,217 B1 | 12/2003 | Herzog, Jr. et al. |
| 6,673,338 B1 | 1/2004 | Arnold et al. |
| 6,673,891 B2 | 1/2004 | Stamler et al. |
| 6,699,846 B2 | 3/2004 | Elliott et al. |
| 6,703,046 B2 | 3/2004 | Fitzhugh et al. |
| 6,706,274 B2 | 3/2004 | Herrmann et al. |
| 6,709,681 B2 | 3/2004 | Benjamin et al. |
| 6,723,703 B2 | 4/2004 | Gaston et al. |
| 6,737,447 B1 | 5/2004 | Smith et al. |
| 6,747,062 B2 | 6/2004 | Murrell |
| 6,750,254 B2 | 6/2004 | Hrabie et al. |
| 6,758,214 B2 | 7/2004 | Fine et al. |
| 6,759,430 B2 | 7/2004 | Anggard et al. |
| 6,780,849 B2 | 8/2004 | Herrmann et al. |
| 6,793,644 B2 | 9/2004 | Stenzler |
| 6,796,966 B2 | 9/2004 | Thomas |
| 6,841,166 B1 | 1/2005 | Zhang et al. |
| 6,855,366 B2 | 2/2005 | Smith et al. |
| 6,875,840 B2 | 4/2005 | Stamler et al. |
| 6,887,485 B2 | 5/2005 | Fitzhugh et al. |
| 6,887,994 B2 | 5/2005 | Stamler et al. |
| 6,894,073 B2 | 5/2005 | Lee et al. |
| 6,896,899 B2 | 5/2005 | Demopolos et al. |
| 6,897,218 B2 | 5/2005 | Casella et al. |
| 6,911,433 B2 | 6/2005 | Saavedra et al. |
| 6,911,478 B2 | 6/2005 | Hrabie et al. |
| 6,946,484 B2 | 9/2005 | Adams et al. |
| 6,949,530 B2 | 9/2005 | Hrabie et al. |
| 6,951,902 B2 | 10/2005 | McDonald et al. |
| 6,964,984 B2 | 11/2005 | Stamler et al. |
| 6,974,801 B2 | 12/2005 | Honda et al. |
| 7,012,098 B2 | 3/2006 | Manning et al. |
| 7,015,347 B2 | 3/2006 | Toone et al. |
| 7,025,869 B2 | 4/2006 | Fine et al. |
| 7,030,238 B2 | 4/2006 | Stamler et al. |
| 7,033,999 B2 | 4/2006 | Stamler et al. |
| 7,040,313 B2 | 5/2006 | Fine et al. |
| 7,048,951 B1 | 5/2006 | Seitz et al. |
| 7,049,308 B2 | 5/2006 | Stamler et al. |
| 7,052,711 B2 | 5/2006 | West et al. |
| 7,070,798 B1 | 7/2006 | Michal et al. |
| 7,081,524 B2 | 7/2006 | Saavedra et al. |
| 7,087,588 B2 | 8/2006 | Del Soldato |
| 7,087,709 B2 | 8/2006 | Stamler et al. |
| 7,122,018 B2 | 10/2006 | Stenzler et al. |
| 7,122,027 B2 | 10/2006 | Trescony et al. |
| 7,122,529 B2 | 10/2006 | Ruane et al. |
| 7,128,904 B2 | 10/2006 | Batchelor et al. |
| 7,135,189 B2 | 11/2006 | Knapp |
| 7,135,498 B1 | 11/2006 | Chopp et al. |

(56) References Cited

U.S. PATENT DOCUMENTS

| | | | |
|---|---|---|---|
| 7,157,500 B2 | 1/2007 | Stamler et al. |
| 7,169,809 B2 | 1/2007 | Berthelette et al. |
| 7,176,237 B2 | 2/2007 | Honda et al. |
| 7,179,475 B1 | 2/2007 | Burnett et al. |
| 7,189,761 B2 | 3/2007 | Gorfine |
| 7,199,154 B2 | 4/2007 | Berthelette et al. |
| 7,204,980 B2 | 4/2007 | Clark |
| 7,226,586 B2 | 6/2007 | Fitzhugh et al. |
| 7,234,079 B2 | 6/2007 | Cheng |
| 7,259,250 B2 | 8/2007 | Stamler et al. |
| 7,279,176 B1 | 10/2007 | West et al. |
| 7,282,519 B2 | 10/2007 | Garvey et al. |
| 7,314,857 B2 | 1/2008 | Madhyastha |
| 7,335,383 B2 | 2/2008 | Meyerhoff et al. |
| 7,345,053 B2 | 3/2008 | Garvey |
| 7,348,319 B2 | 3/2008 | Hrabie et al. |
| 7,364,585 B2 | 4/2008 | Weber |
| 7,396,829 B2 | 7/2008 | Garvey et al. |
| 7,417,109 B2 | 8/2008 | Stamler et al. |
| 7,425,218 B2 | 9/2008 | Keefer et al. |
| 7,432,301 B2 | 10/2008 | Gaston et al. |
| 7,452,916 B2 | 11/2008 | Cooke |
| 7,468,435 B2 | 12/2008 | Waterhouse et al. |
| 7,485,324 B2 | 2/2009 | Miller et al. |
| 7,520,866 B2 | 4/2009 | Stenzler et al. |
| 7,531,164 B2 | 5/2009 | Daaka et al. |
| 7,569,559 B2 | 8/2009 | Arnold et al. |
| 7,582,623 B2 | 9/2009 | Mascharak |
| 7,595,313 B2 | 9/2009 | Garvey et al. |
| 7,622,501 B2 | 11/2009 | Dufresne et al. |
| 7,622,502 B2 | 11/2009 | Berthelette et al. |
| 7,645,748 B2 | 1/2010 | Orchansky et al. |
| 7,645,749 B2 | 1/2010 | Orchansky et al. |
| 7,651,697 B2 | 1/2010 | West et al. |
| 7,655,423 B2 | 2/2010 | Chopp et al. |
| 7,678,391 B2 | 3/2010 | Graham et al. |
| 7,678,830 B2 | 3/2010 | Honda et al. |
| 7,696,247 B2 | 4/2010 | Herrmann et al. |
| 7,704,518 B2 | 4/2010 | Tamarkin et al. |
| 7,745,656 B2 | 6/2010 | Toone et al. |
| 7,763,283 B2 | 7/2010 | Batchelor et al. |
| 7,785,616 B2 | 8/2010 | Stamler et al. |
| 7,795,286 B2 | 9/2010 | Lucet-Levannier |
| 7,799,335 B2 | 9/2010 | Herrmann et al. |
| 7,807,716 B2 | 10/2010 | Farber |
| 7,811,600 B2 | 10/2010 | Cheng et al. |
| 7,820,284 B2 | 10/2010 | Terry |
| 7,829,553 B2 | 11/2010 | Arnold et al. |
| 7,838,023 B2 | 11/2010 | Garvey et al. |
| 7,846,400 B2 | 12/2010 | Hyde et al. |
| 7,862,598 B2 | 1/2011 | Hyde et al. |
| 7,892,198 B2 | 2/2011 | Stenzler |
| 7,897,399 B2 | 3/2011 | Hyde et al. |
| 7,928,079 B2 | 4/2011 | Hrabie et al. |
| 7,928,096 B2 | 4/2011 | Waterhouse et al. |
| 7,947,299 B2 | 5/2011 | Knapp |
| 7,972,137 B2 | 7/2011 | Rosen |
| 7,975,699 B2 | 7/2011 | Hyde et al. |
| 8,003,811 B2 | 8/2011 | Almirante |
| 8,017,074 B2 | 9/2011 | Arnold |
| 8,021,679 B2 | 9/2011 | Chen |
| 8,034,384 B2 | 10/2011 | Meyerhoff |
| 8,043,246 B2 | 10/2011 | Av-Gay et al. |
| 8,241,650 B2 | 8/2012 | Peters |
| 8,343,945 B2 | 1/2013 | Tamarkin et al. |
| 8,362,091 B2 | 1/2013 | Tamarkin et al. |
| 8,486,374 B2 | 7/2013 | Tamarkin et al. |
| 8,617,100 B2 | 12/2013 | Eini et al. |
| 8,636,982 B2 | 1/2014 | Tamarkin et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 9,101,662 B2 | 8/2015 | Tamarkin et al. |
| 9,161,916 B2 | 10/2015 | Tamarkin et al. |
| 9,265,725 B2 | 2/2016 | Tamarkin et al. |
| 9,320,705 B2 | 4/2016 | Tamarkin et al. |
| 2001/0012851 A1 | 8/2001 | Lundy et al. |
| 2001/0025057 A1 | 9/2001 | Gorfine |
| 2001/0038832 A1 | 11/2001 | Bonavida et al. |
| 2001/0053772 A1 | 12/2001 | Bonavida et al. |
| 2002/0013304 A1* | 1/2002 | Wilson et al. ............... 514/177 |
| 2002/0018757 A1 | 2/2002 | Harichian et al. |
| 2002/0028223 A1* | 3/2002 | Vatter et al. ................ 424/401 |
| 2002/0028851 A1 | 3/2002 | Bianchi et al. |
| 2002/0049157 A1 | 4/2002 | Wu et al. |
| 2002/0061879 A1 | 5/2002 | Garvey et al. |
| 2002/0068365 A1 | 6/2002 | Kuhrts |
| 2002/0090401 A1 | 7/2002 | Tucker et al. |
| 2002/0115586 A1 | 8/2002 | Enikolopov |
| 2002/0122929 A1 | 9/2002 | Simpson et al. |
| 2002/0132234 A1 | 9/2002 | Moskowitz |
| 2002/0133040 A1 | 9/2002 | Woo et al. |
| 2002/0136763 A1 | 9/2002 | Demopoulos et al. |
| 2002/0138051 A1 | 9/2002 | Hole et al. |
| 2002/0143007 A1 | 10/2002 | Garvey et al. |
| 2002/0143062 A1 | 10/2002 | Lopez-Berestein et al. |
| 2002/0155174 A1 | 10/2002 | Benjamin et al. |
| 2002/0161042 A1 | 10/2002 | Gorfine |
| 2003/0027844 A1 | 2/2003 | Soldato |
| 2003/0039697 A1 | 2/2003 | Zhao et al. |
| 2003/0050305 A1 | 3/2003 | Tejada |
| 2003/0072783 A1 | 4/2003 | Stamler et al. |
| 2003/0093143 A1 | 5/2003 | Zhao et al. |
| 2003/0134779 A1 | 7/2003 | Diarra et al. |
| 2003/0170674 A1 | 9/2003 | Moskowitz |
| 2003/0203915 A1 | 10/2003 | Fang et al. |
| 2003/0219854 A1 | 11/2003 | Guarna et al. |
| 2004/0009238 A1 | 1/2004 | Miller et al. |
| 2004/0013747 A1 | 1/2004 | Tucker et al. |
| 2004/0033480 A1 | 2/2004 | Wong |
| 2004/0037836 A1 | 2/2004 | Stamler et al. |
| 2004/0037897 A1 | 2/2004 | Benjamin et al. |
| 2004/0043068 A1 | 3/2004 | Tedeschi et al. |
| 2004/0076582 A1 | 4/2004 | Dimatteo et al. |
| 2004/0082659 A1 | 4/2004 | Cooke et al. |
| 2004/0105898 A1 | 6/2004 | Benjamin et al. |
| 2004/0110691 A1 | 6/2004 | Stamler |
| 2004/0131703 A1 | 7/2004 | Bach et al. |
| 2004/0143010 A1 | 7/2004 | Esteve-Soler et al. |
| 2004/0147598 A1 | 7/2004 | Haj-Yehia |
| 2004/0157936 A1 | 8/2004 | Burnett et al. |
| 2004/0228889 A1 | 11/2004 | Cals-Grierson |
| 2004/0254419 A1 | 12/2004 | Wang et al. |
| 2004/0265244 A1 | 12/2004 | Rosen |
| 2005/0036949 A1 | 2/2005 | Tucker et al. |
| 2005/0037093 A1 | 2/2005 | Benjamin |
| 2005/0038473 A1 | 2/2005 | Tamarkin et al. |
| 2005/0054714 A1 | 3/2005 | Munoz et al. |
| 2005/0065161 A1 | 3/2005 | Garvey et al. |
| 2005/0069595 A1 | 3/2005 | Chen et al. |
| 2005/0074506 A1 | 4/2005 | Natan et al. |
| 2005/0079132 A1 | 4/2005 | Wang et al. |
| 2005/0080021 A1 | 4/2005 | Tucker et al. |
| 2005/0080024 A1 | 4/2005 | Tucker et al. |
| 2005/0131064 A1 | 6/2005 | Gaston et al. |
| 2005/0142217 A1 | 6/2005 | Adams et al. |
| 2005/0142218 A1 | 6/2005 | Tucker et al. |
| 2005/0152891 A1 | 7/2005 | Toone et al. |
| 2005/0165452 A1 | 7/2005 | Sigg et al. |
| 2005/0171006 A1 | 8/2005 | Bunting et al. |
| 2005/0171199 A1 | 8/2005 | Murrell |
| 2005/0187222 A1 | 8/2005 | Garvey et al. |
| 2005/0220838 A1 | 10/2005 | Zhao et al. |
| 2005/0232869 A1 | 10/2005 | Tamarkin et al. |
| 2005/0245492 A1 | 11/2005 | Lephart et al. |
| 2005/0249818 A1 | 11/2005 | Sawan et al. |
| 2005/0265958 A1 | 12/2005 | West et al. |
| 2005/0271596 A1 | 12/2005 | Friedman et al. |
| 2005/0281867 A1 | 12/2005 | Kahn et al. |
| 2006/0008529 A1 | 1/2006 | Meyerhoff et al. |
| 2006/0009431 A1 | 1/2006 | Earl et al. |
| 2006/0035854 A1 | 2/2006 | Goldstein et al. |
| 2006/0039950 A1 | 2/2006 | Zhou et al. |
| 2006/0058363 A1 | 3/2006 | Wang et al. |

(56) References Cited

U.S. PATENT DOCUMENTS

| | | |
|---|---|---|
| 2006/0067909 A1 | 3/2006 | West et al. |
| 2006/0095120 A1 | 5/2006 | Herrmann |
| 2006/0100159 A1 | 5/2006 | Stamler et al. |
| 2006/0142183 A1 | 6/2006 | Diarra et al. |
| 2006/0147553 A1 | 7/2006 | Miller et al. |
| 2006/0147904 A1 | 7/2006 | Wong |
| 2006/0153904 A1 | 7/2006 | Smith et al. |
| 2006/0155260 A1 | 7/2006 | Blott et al. |
| 2006/0159726 A1 | 7/2006 | Shell |
| 2006/0160897 A1 | 7/2006 | Pelicci et al. |
| 2006/0172018 A1 | 8/2006 | Fine et al. |
| 2006/0198831 A1 | 9/2006 | Stamler et al. |
| 2006/0211601 A1 | 9/2006 | Stamler et al. |
| 2006/0269620 A1 | 11/2006 | Morris et al. |
| 2006/0275218 A1 | 12/2006 | Tamarkin et al. |
| 2006/0286158 A1 | 12/2006 | Calvert Murrell et al. |
| 2006/0286159 A1 | 12/2006 | Calvert Murrell et al. |
| 2007/0003538 A1 | 1/2007 | Madhyastha |
| 2007/0014686 A1 | 1/2007 | Arnold et al. |
| 2007/0014733 A1 | 1/2007 | O'Donnell et al. |
| 2007/0014828 A1 | 1/2007 | Fitzhugh et al. |
| 2007/0037821 A1 | 2/2007 | Garvey et al. |
| 2007/0048344 A1 | 3/2007 | Yahiaoui et al. |
| 2007/0053952 A1 | 3/2007 | Chen et al. |
| 2007/0053955 A1 | 3/2007 | Larson et al. |
| 2007/0053966 A1 | 3/2007 | Ang et al. |
| 2007/0059351 A1 | 3/2007 | Murrell et al. |
| 2007/0086954 A1 | 4/2007 | Miller |
| 2007/0087025 A1 | 4/2007 | Fitzhugh et al. |
| 2007/0088345 A1 | 4/2007 | Larson et al. |
| 2007/0089739 A1 | 4/2007 | Fine et al. |
| 2007/0116785 A1 | 5/2007 | Miller |
| 2007/0129690 A1 | 6/2007 | Rosenblatt et al. |
| 2007/0148136 A1 | 6/2007 | Whitlock |
| 2007/0154570 A1 | 7/2007 | Miller et al. |
| 2007/0166227 A1 | 7/2007 | Liu et al. |
| 2007/0166255 A1* | 7/2007 | Gupta .................... 424/70.1 |
| 2007/0172469 A1 | 7/2007 | Clark |
| 2007/0191377 A1 | 8/2007 | Worcel |
| 2007/0196327 A1 | 8/2007 | Kalivretenos et al. |
| 2007/0197543 A1 | 8/2007 | Esteve-Soler et al. |
| 2007/0202155 A1 | 8/2007 | Ang et al. |
| 2007/0203242 A1 | 8/2007 | Calton |
| 2007/0207179 A1 | 9/2007 | Andersen et al. |
| 2007/0219208 A1 | 9/2007 | Kalyanaraman et al. |
| 2007/0225250 A1 | 9/2007 | Brown |
| 2007/0239107 A1 | 10/2007 | Lundberg et al. |
| 2007/0243262 A1 | 10/2007 | Hurley et al. |
| 2007/0248676 A1 | 10/2007 | Stamler et al. |
| 2007/0264225 A1 | 11/2007 | Cheng et al. |
| 2007/0270348 A1 | 11/2007 | Kahn et al. |
| 2007/0275100 A1 | 11/2007 | Miller |
| 2007/0292359 A1 | 12/2007 | Friedman et al. |
| 2007/0292461 A1 | 12/2007 | Tamarkin et al. |
| 2008/0025972 A1 | 1/2008 | Daaka et al. |
| 2008/0031907 A1 | 2/2008 | Tamarkin et al. |
| 2008/0033334 A1 | 2/2008 | Gurtner et al. |
| 2008/0039521 A1 | 2/2008 | Yasuda et al. |
| 2008/0044444 A1 | 2/2008 | Tamarkin et al. |
| 2008/0045909 A1 | 2/2008 | Fossel |
| 2008/0063607 A1 | 3/2008 | Tamarkin et al. |
| 2008/0069779 A1 | 3/2008 | Tamarkin et al. |
| 2008/0069848 A1 | 3/2008 | Peters |
| 2008/0069863 A1 | 3/2008 | Peters |
| 2008/0069905 A1 | 3/2008 | Peters |
| 2008/0071206 A1 | 3/2008 | Peters |
| 2008/0089956 A1 | 4/2008 | Da et al. |
| 2008/0138296 A1 | 6/2008 | Tamarkin et al. |
| 2008/0139450 A1 | 6/2008 | Madhyastha et al. |
| 2008/0145449 A1 | 6/2008 | Stamler |
| 2008/0152596 A1 | 6/2008 | Friedman et al. |
| 2008/0166303 A1 | 7/2008 | Tamarkin et al. |
| 2008/0171021 A1 | 7/2008 | Bach et al. |
| 2008/0171351 A1 | 7/2008 | Smith |
| 2008/0175881 A1 | 7/2008 | Ippoliti et al. |
| 2008/0182797 A1 | 7/2008 | Nudler et al. |
| 2008/0193385 A1 | 8/2008 | Maibach |
| 2008/0193566 A1 | 8/2008 | Miller et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0207491 A1 | 8/2008 | Diarra et al. |
| 2008/0207713 A1 | 8/2008 | Wang et al. |
| 2008/0214646 A1 | 9/2008 | Knaus et al. |
| 2008/0226751 A1 | 9/2008 | Tucker et al. |
| 2008/0241208 A1 | 10/2008 | Shanley et al. |
| 2008/0253973 A1 | 10/2008 | Tamarkin et al. |
| 2008/0260655 A1 | 10/2008 | Tamarkin et al. |
| 2008/0275093 A1 | 11/2008 | Garvey et al. |
| 2008/0280984 A1 | 11/2008 | Fossel |
| 2008/0286321 A1 | 11/2008 | Reneker et al. |
| 2008/0287861 A1 | 11/2008 | Stenzler et al. |
| 2008/0292560 A1 | 11/2008 | Tamarkin et al. |
| 2008/0299220 A1 | 12/2008 | Tamarkin et al. |
| 2008/0306012 A1 | 12/2008 | Hrabie et al. |
| 2008/0311163 A1 | 12/2008 | Peters |
| 2008/0317626 A1 | 12/2008 | Arnold et al. |
| 2008/0317679 A1 | 12/2008 | Tamarkin et al. |
| 2009/0004298 A1 | 1/2009 | Gaston et al. |
| 2009/0010989 A1 | 1/2009 | Peters |
| 2009/0018091 A1 | 1/2009 | Ellis et al. |
| 2009/0028966 A1 | 1/2009 | Chen et al. |
| 2009/0029028 A1 | 1/2009 | Garcin et al. |
| 2009/0036491 A1 | 2/2009 | Tucker et al. |
| 2009/0041680 A1 | 2/2009 | Tamarkin et al. |
| 2009/0042819 A1 | 2/2009 | Ellis et al. |
| 2009/0048219 A1 | 2/2009 | Garvey |
| 2009/0068118 A1 | 3/2009 | Eini et al. |
| 2009/0068248 A1 | 3/2009 | Waterhouse et al. |
| 2009/0069449 A1 | 3/2009 | Smith et al. |
| 2009/0081279 A1 | 3/2009 | Jezek et al. |
| 2009/0088411 A1 | 4/2009 | Renzi et al. |
| 2009/0093510 A1 | 4/2009 | Clementi et al. |
| 2009/0098187 A1 | 4/2009 | Peters et al. |
| 2009/0108777 A1 | 4/2009 | Hyde et al. |
| 2009/0110612 A1 | 4/2009 | Hyde et al. |
| 2009/0110712 A1 | 4/2009 | Hyde et al. |
| 2009/0110933 A1 | 4/2009 | Hyde et al. |
| 2009/0110958 A1 | 4/2009 | Hyde et al. |
| 2009/0112055 A1 | 4/2009 | Hyde et al. |
| 2009/0112193 A1 | 4/2009 | Hyde et al. |
| 2009/0112197 A1 | 4/2009 | Hyde et al. |
| 2009/0118819 A1 | 5/2009 | Merz et al. |
| 2009/0123528 A1 | 5/2009 | Fossel |
| 2009/0130029 A1 | 5/2009 | Tamarkin et al. |
| 2009/0131342 A1 | 5/2009 | Ellis |
| 2009/0136410 A1 | 5/2009 | Smith |
| 2009/0137683 A1 | 5/2009 | Yasuda et al. |
| 2009/0143417 A1 | 6/2009 | Smith et al. |
| 2009/0148482 A1 | 6/2009 | Peters |
| 2009/0175799 A1 | 7/2009 | Tamarkin et al. |
| 2009/0186859 A1 | 7/2009 | Velázquez et al. |
| 2009/0191284 A1 | 7/2009 | Conoci et al. |
| 2009/0196930 A1 | 8/2009 | Surber et al. |
| 2009/0197964 A1 | 8/2009 | Summar et al. |
| 2009/0203653 A1 | 8/2009 | Garvey |
| 2009/0214618 A1* | 8/2009 | Schoenfisch et al. ........ 424/426 |
| 2009/0214624 A1 | 8/2009 | Smith et al. |
| 2009/0214674 A1 | 8/2009 | Barraud et al. |
| 2009/0215838 A1 | 8/2009 | Garvey et al. |
| 2009/0221536 A1 | 9/2009 | Fossel |
| 2009/0222088 A1 | 9/2009 | Chen et al. |
| 2009/0226504 A1 | 9/2009 | Peters |
| 2009/0232863 A1 | 9/2009 | Cheng et al. |
| 2009/0232868 A1 | 9/2009 | Chen et al. |
| 2009/0255536 A1 | 10/2009 | Av-Gay et al. |
| 2009/0263416 A1 | 10/2009 | Dawson et al. |
| 2009/0264398 A1 | 10/2009 | Bauer |
| 2009/0270509 A1 | 10/2009 | Arnold et al. |
| 2009/0287072 A1 | 11/2009 | Meyerhoff et al. |
| 2009/0297634 A1* | 12/2009 | Friedman et al. ............ 424/718 |
| 2009/0304815 A1 | 12/2009 | Cossu et al. |
| 2009/0317885 A1 | 12/2009 | Mascharak |
| 2010/0003338 A1 | 1/2010 | Hubbell et al. |

(56) References Cited

U.S. PATENT DOCUMENTS

| | | |
|---|---|---|
| 2010/0015253 A1 | 1/2010 | Benjamin |
| 2010/0016767 A1 | 1/2010 | Jones et al. |
| 2010/0016790 A1 | 1/2010 | Peters |
| 2010/0021506 A1 | 1/2010 | Jones |
| 2010/0040703 A1 | 2/2010 | Miller et al. |
| 2010/0062055 A1 | 3/2010 | Herrmann et al. |
| 2010/0076162 A1 | 3/2010 | Ameer et al. |
| 2010/0086530 A1 | 4/2010 | Martinov |
| 2010/0087370 A1 | 4/2010 | Jain et al. |
| 2010/0098733 A1 | 4/2010 | Stasko |
| 2010/0099729 A1 | 4/2010 | Almirante et al. |
| 2010/0112033 A1 | 5/2010 | Ganzarolli de Oliveira et al. |
| 2010/0112095 A1 | 5/2010 | Morris et al. |
| 2010/0129474 A1 | 5/2010 | Benjamin et al. |
| 2010/0152683 A1 | 6/2010 | Lindgren et al. |
| 2010/0159119 A1 | 6/2010 | Chen et al. |
| 2010/0166603 A1 | 7/2010 | Opie |
| 2010/0178319 A1 | 7/2010 | Lindgren et al. |
| 2010/0184992 A1 | 7/2010 | Toone et al. |
| 2010/0196517 A1 | 8/2010 | Fossel |
| 2010/0197702 A1 | 8/2010 | Hellberg et al. |
| 2010/0197802 A1 | 8/2010 | Jezek et al. |
| 2010/0209469 A1 | 8/2010 | Bezwada |
| 2010/0210745 A1 | 8/2010 | McDaniel et al. |
| 2010/0221195 A1 | 9/2010 | Tamarkin et al. |
| 2010/0221308 A1 | 9/2010 | Madhyastha et al. |
| 2010/0233304 A1 | 9/2010 | Pan |
| 2010/0239512 A1 | 9/2010 | Morris et al. |
| 2010/0247611 A1 | 9/2010 | Balkus, Jr. et al. |
| 2010/0247680 A1 | 9/2010 | Szabo |
| 2010/0255062 A1 | 10/2010 | Kalivretenos et al. |
| 2010/0256755 A1 | 10/2010 | Chen et al. |
| 2010/0261930 A1 | 10/2010 | Honda et al. |
| 2010/0262238 A1 | 10/2010 | Chen et al. |
| 2010/0266510 A1 | 10/2010 | Tamarkin et al. |
| 2010/0268149 A1 | 10/2010 | Av-Gay et al. |
| 2010/0276284 A1 | 11/2010 | Meyerhoff et al. |
| 2010/0280122 A1 | 11/2010 | Fossel |
| 2010/0285100 A1 | 11/2010 | Balkus, Jr. et al. |
| 2010/0286285 A1 | 11/2010 | Barthez et al. |
| 2010/0297200 A1 | 11/2010 | Schoenfisch et al. |
| 2010/0303891 A1 | 12/2010 | Lee et al. |
| 2010/0310476 A1 | 12/2010 | Tamarkin et al. |
| 2010/0311780 A1 | 12/2010 | Farber |
| 2010/0323036 A1 | 12/2010 | Fine |
| 2010/0324107 A1 | 12/2010 | Dos Santos et al. |
| 2010/0331542 A1 | 12/2010 | Smith |
| 2010/0331968 A1 | 12/2010 | Morris et al. |
| 2011/0008815 A1 | 1/2011 | Stamler et al. |
| 2011/0033437 A1 | 2/2011 | Smith et al. |
| 2011/0038965 A1 | 2/2011 | McKay et al. |
| 2011/0045037 A1 | 2/2011 | Tamarkin et al. |
| 2011/0046182 A1 | 2/2011 | Gilmer et al. |
| 2011/0059036 A1 | 3/2011 | Arnold et al. |
| 2011/0059189 A1 | 3/2011 | Cisneros |
| 2011/0065783 A1 | 3/2011 | O'Donnell et al. |
| 2011/0070318 A1 | 3/2011 | Jezek et al. |
| 2011/0071168 A1 | 3/2011 | Chopp et al. |
| 2011/0076313 A1 | 3/2011 | Av-Gay et al. |
| 2011/0086234 A1 | 4/2011 | Stasko et al. |
| 2011/0097279 A1 | 4/2011 | Tamarkin et al. |
| 2011/0104240 A1 | 5/2011 | Jones et al. |
| 2011/0106000 A1 | 5/2011 | Jones et al. |
| 2011/0212033 A1 | 9/2011 | Tamarkin et al. |
| 2012/0136323 A1* | 5/2012 | Stasko et al. ............... 604/290 |
| 2012/0141384 A1 | 6/2012 | Tamarkin et al. |
| 2012/0237453 A1 | 9/2012 | Tamarkin et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0310533 A1 | 11/2013 | Bao et al. |
| 2013/0344334 A1 | 12/2013 | Schoenfisch et al. |
| 2014/0017121 A1 | 1/2014 | Schoenfisch et al. |
| 2014/0057001 A1 | 2/2014 | Bauman et al. |
| 2014/0065200 A1 | 3/2014 | Schoenfisch et al. |
| 2014/0105986 A1 | 4/2014 | Doxey et al. |
| 2014/0107071 A1 | 4/2014 | Kougoulos et al. |
| 2014/0134321 A1 | 5/2014 | Stasko et al. |
| 2014/0171395 A1 | 6/2014 | Schoenfisch et al. |
| 2014/0193502 A1 | 7/2014 | Tamarkin et al. |
| 2014/0242023 A1 | 8/2014 | Doxey et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2014/0369949 A1 | 12/2014 | Peters |
| 2015/0017103 A1 | 1/2015 | Tamarkin et al. |
| 2015/0024052 A1 | 1/2015 | Doxey |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2015/0141606 A1 | 5/2015 | Bao et al. |
| 2015/0182543 A1 | 7/2015 | Schoenfisch et al. |
| 2015/0225488 A1 | 8/2015 | Schoenfisch et al. |

FOREIGN PATENT DOCUMENTS

| | | | |
|---|---|---|---|
| EP | 0 746 327 B1 | 4/2004 | |
| EP | 0 724 436 B1 | 7/2004 | |
| EP | 1 411 908 B1 | 5/2005 | |
| EP | 1 163 528 B1 | 11/2005 | |
| EP | 1 681 068 A1 | 7/2006 | |
| EP | 1 690 532 A1 | 8/2006 | |
| EP | 1 690 554 A1 | 8/2006 | |
| EP | 1 690 557 A1 | 8/2006 | |
| EP | 1 690 558 A1 | 8/2006 | |
| EP | 1 700 611 A1 | 9/2006 | |
| EP | 1 704 876 A1 | 9/2006 | |
| EP | 1 704 877 A1 | 9/2006 | |
| EP | 1 704 879 A1 | 9/2006 | |
| EP | 1 707 224 A1 | 10/2006 | |
| EP | 1 728 438 A1 | 12/2006 | |
| EP | 1 731 176 A1 | 12/2006 | |
| EP | 1 757 278 A1 | 2/2007 | |
| EP | 1 764 119 A1 | 3/2007 | |
| EP | 1 790 335 A1 | 5/2007 | |
| EP | 1 861 130 B1 | 9/2008 | |
| EP | 1 343 547 B1 | 4/2009 | |
| EP | 1 871 433 B1 | 4/2009 | |
| EP | 1 161 248 B1 | 5/2009 | |
| EP | 1 846 058 B1 | 7/2009 | |
| EP | 2 119 459 A1 | 11/2009 | |
| EP | 2 142 179 A1 | 1/2010 | |
| EP | 2 142 181 A1 | 1/2010 | |
| EP | 1 917 005 B1 | 9/2010 | |
| IL | WO 2008110872 A2 * | 9/2008 | ........... A61K 9/0014 |
| WO | WO 93/10754 A1 | 6/1993 | |
| WO | WO 95/07691 A1 | 3/1995 | |
| WO | WO 95/10267 A1 | 4/1995 | |
| WO | WO 95/12394 A1 | 5/1995 | |
| WO | WO 95/19767 A1 | 7/1995 | |
| WO | WO 95/22335 A1 | 8/1995 | |
| WO | WO 95/32715 A1 | 12/1995 | |
| WO | WO 96/08966 A1 | 3/1996 | |
| WO | WO 96/13164 A1 | 5/1996 | |
| WO | WO 96/14844 A1 | 5/1996 | |
| WO | WO 96/15781 A1 | 5/1996 | |
| WO | WO 96/15797 A1 | 5/1996 | |
| WO | WO 96/27386 A1 | 9/1996 | |
| WO | WO 96/32118 A1 | 10/1996 | |
| WO | WO 96/32136 A1 | 10/1996 | |
| WO | WO 96/33757 A1 | 10/1996 | |
| WO | WO 96/35416 A1 | 11/1996 | |
| WO | WO 96/35416 AI | 11/1996 | |
| WO | WO 97/16983 A1 | 5/1997 | |
| WO | WO 97/31654 A1 | 9/1997 | |
| WO | WO 97/34014 A1 | 9/1997 | |
| WO | WO 97/47254 A1 | 12/1997 | |
| WO | WO 98/05689 A1 | 2/1998 | |
| WO | WO 98/06389 A1 | 2/1998 | |
| WO | WO 98/08482 A2 | 3/1998 | |
| WO | WO 98/08482 A3 | 3/1998 | |
| WO | WO 98/08496 A1 | 3/1998 | |
| WO | WO 98/13358 A1 | 4/1998 | |

(56) References Cited

FOREIGN PATENT DOCUMENTS

| | | |
|---|---|---|
| WO | WO 98/19996 A1 | 5/1998 |
| WO | WO 98/20015 A1 | 5/1998 |
| WO | WO 98/22090 A1 | 5/1998 |
| WO | WO 98/29101 A1 | 7/1998 |
| WO | WO 98/42661 A1 | 10/1998 |
| WO | WO 99/00070 A1 | 1/1999 |
| WO | WO 99/01427 A2 | 1/1999 |
| WO | WO 99/18949 A1 | 4/1999 |
| WO | WO 99/22729 A1 | 5/1999 |
| WO | WO 99/33823 A1 | 7/1999 |
| WO | WO 99/37616 A1 | 7/1999 |
| WO | WO 99/44595 A2 | 9/1999 |
| WO | WO 99/44595 A3 | 9/1999 |
| WO | WO 99/51221 A1 | 10/1999 |
| WO | WO 99/67210 A1 | 12/1999 |
| WO | WO 99/67296 A1 | 12/1999 |
| WO | WO 00/03640 A1 | 1/2000 |
| WO | WO 00/06151 A1 | 2/2000 |
| WO | WO 00/30658 A1 | 6/2000 |
| WO | WO 00/33877 A1 | 6/2000 |
| WO | WO 00/56333 A1 | 9/2000 |
| WO | WO 00/59304 A1 | 10/2000 |
| WO | WO 00/76318 A1 | 12/2000 |
| WO | WO 01/12067 A1 | 2/2001 |
| WO | WO 01/15738 A2 | 3/2001 |
| WO | WO 01/15738 A3 | 3/2001 |
| WO | WO 01/26702 A2 | 4/2001 |
| WO | WO 01/26702 A3 | 4/2001 |
| WO | WO 01/45732 A2 | 6/2001 |
| WO | WO 01/45732 A3 | 6/2001 |
| WO | WO 01/70199 A1 | 9/2001 |
| WO | WO 01/85227 A2 | 11/2001 |
| WO | WO 01/85227 A3 | 11/2001 |
| WO | WO 01/89572 A1 | 11/2001 |
| WO | WO 02/17880 A2 | 3/2002 |
| WO | WO 02/17880 A3 | 3/2002 |
| WO | WO 02/17881 A2 | 3/2002 |
| WO | WO 02/17881 A3 | 3/2002 |
| WO | WO 02/20026 A2 | 3/2002 |
| WO | WO 02/20026 A3 | 3/2002 |
| WO | WO 02/32418 A1 | 4/2002 |
| WO | WO 02/34705 A2 | 5/2002 |
| WO | WO 02/43786 A2 | 6/2002 |
| WO | WO 02/43786 A3 | 6/2002 |
| WO | WO 02/47675 A1 | 6/2002 |
| WO | WO 02/051353 A2 | 7/2002 |
| WO | WO 02/051353 A3 | 7/2002 |
| WO | WO 02/056864 A2 | 7/2002 |
| WO | WO 02/056864 A3 | 7/2002 |
| WO | WO 02/056874 A2 | 7/2002 |
| WO | WO 02/056904 A1 | 7/2002 |
| WO | WO 02/070496 A1 | 9/2002 |
| WO | WO 02/076395 A2 | 10/2002 |
| WO | WO 02/076395 A3 | 10/2002 |
| WO | WO 03/004097 A1 | 1/2003 |
| WO | WO 03/006427 A1 | 1/2003 |
| WO | WO 03/015605 A2 | 2/2003 |
| WO | WO 03/015605 A3 | 2/2003 |
| WO | WO 03/017989 A1 | 3/2003 |
| WO | WO 03/026717 A1 | 4/2003 |
| WO | WO 03/030659 A1 | 4/2003 |
| WO | WO 03/041713 A1 | 5/2003 |
| WO | WO 03/047636 A2 | 6/2003 |
| WO | WO 03/047636 A3 | 6/2003 |
| WO | WO 03/080039 A1 | 10/2003 |
| WO | WO 03/092763 A1 | 11/2003 |
| WO | WO 03/095398 A2 | 11/2003 |
| WO | WO 03/095398 A3 | 11/2003 |
| WO | WO 2004/009066 A1 | 1/2004 |
| WO | WO 2004/009253 A1 | 1/2004 |
| WO | WO 2004/011421 A1 | 2/2004 |
| WO | WO 2004/012874 A1 | 2/2004 |
| WO | WO 2004/037798 A1 | 5/2004 |
| WO | WO 2004/039313 A2 | 5/2004 |
| WO | WO 2004/039313 A3 | 5/2004 |
| WO | WO 2004/060283 A2 | 7/2004 |
| WO | WO 2004/064767 A2 | 8/2004 |
| WO | WO 2004/064767 A3 | 8/2004 |
| WO | WO 2004/087212 A2 | 10/2004 |
| WO | WO 2004/098538 A2 | 11/2004 |
| WO | WO 2004/098538 A3 | 11/2004 |
| WO | WO 2005/003032 A1 | 1/2005 |
| WO | WO 2005/004984 A1 | 1/2005 |
| WO | WO 2005/011575 A2 | 2/2005 |
| WO | WO 2005/011575 A2 | 2/2005 |
| WO | WO 2005/011575 A3 | 2/2005 |
| WO | WO 2005/011575 A3 | 2/2005 |
| WO | WO 2005/030118 A2 | 4/2005 |
| WO | WO 2005/030118 A3 | 4/2005 |
| WO | WO 2005/030135 A2 | 4/2005 |
| WO | WO 2005/030135 A3 | 4/2005 |
| WO | WO 2005/030147 A2 | 4/2005 |
| WO | WO 2005/030147 A3 | 4/2005 |
| WO | WO 2005/034860 A2 | 4/2005 |
| WO | WO 2005/034860 A3 | 4/2005 |
| WO | WO 2005/039664 A2 | 5/2005 |
| WO | WO 2005/039664 A3 | 5/2005 |
| WO | WO 2005/067986 A1 | 7/2005 |
| WO | WO 2005/070006 A2 | 8/2005 |
| WO | WO 2005/070006 A3 | 8/2005 |
| WO | WO 2005/070008 A2 | 8/2005 |
| WO | WO 2005/070008 A3 | 8/2005 |
| WO | WO 2005/070874 A1 | 8/2005 |
| WO | WO 2005/070883 A1 | 8/2005 |
| WO | WO 2005/072819 A1 | 8/2005 |
| WO | WO 2005/077962 A2 | 8/2005 |
| WO | WO 2005/077962 A3 | 8/2005 |
| WO | WO 2005/081752 A2 | 9/2005 |
| WO | WO 2005/081752 A3 | 9/2005 |
| WO | WO 2005/081964 A2 | 9/2005 |
| WO | WO 2005/094913 A1 | 10/2005 |
| WO | WO 2005/102282 A1 | 11/2005 |
| WO | WO 2005/107384 A2 | 11/2005 |
| WO | WO 2005/107384 A3 | 11/2005 |
| WO | WO 2005/112954 A1 | 12/2005 |
| WO | WO 2005/115440 A2 | 12/2005 |
| WO | WO 2005/115440 A3 | 12/2005 |
| WO | WO 2005/120493 A1 | 12/2005 |
| WO | WO 2006/023693 A2 | 3/2006 |
| WO | WO 2006/023693 A3 | 3/2006 |
| WO | WO 2006/037105 A2 | 4/2006 |
| WO | WO 2006/037105 A3 | 4/2006 |
| WO | WO 2006/041855 A2 | 4/2006 |
| WO | WO 2006/041855 A3 | 4/2006 |
| WO | WO 2006/045639 A1 | 5/2006 |
| WO | WO 2006/055542 A2 | 5/2006 |
| WO | WO 2006/055542 A3 | 5/2006 |
| WO | WO 2006/058318 A2 | 6/2006 |
| WO | WO 2006/064056 A2 | 6/2006 |
| WO | WO 2006/066362 A1 | 6/2006 |
| WO | WO 2006/084909 A1 | 8/2006 |
| WO | WO 2006/084910 A1 | 8/2006 |
| WO | WO 2006/084911 A1 | 8/2006 |
| WO | WO 2006/084912 A1 | 8/2006 |
| WO | WO 2006/084913 A1 | 8/2006 |
| WO | WO 2006/084914 A1 | 8/2006 |
| WO | WO 2006/100155 A1 | 8/2006 |
| WO | WO 2006/095193 A2 | 9/2006 |
| WO | WO 2006/095193 A3 | 9/2006 |
| WO | WO 2006/096572 A1 | 9/2006 |
| WO | WO 2006/097348 A1 | 9/2006 |
| WO | WO 2006/099058 A2 | 9/2006 |
| WO | WO 2006/099058 A3 | 9/2006 |
| WO | WO 2006/100154 A1 | 9/2006 |
| WO | WO 2006/100156 A2 | 9/2006 |
| WO | WO 2006/100156 A3 | 9/2006 |
| WO | WO 2006/122960 A1 | 11/2006 |
| WO | WO 2006/122961 A1 | 11/2006 |
| WO | WO 2006/125016 A1 | 11/2006 |
| WO | WO 2006/125262 A1 | 11/2006 |
| WO | WO 2006/127591 A2 | 11/2006 |
| WO | WO 2006/127591 A3 | 11/2006 |
| WO | WO 2006/128121 A2 | 11/2006 |
| WO | WO 2006/128742 A2 | 12/2006 |

(56) References Cited

FOREIGN PATENT DOCUMENTS

| | | |
|---|---|---|
| WO | WO 2006/128742 A3 | 12/2006 |
| WO | WO 2006/128743 A1 | 12/2006 |
| WO | WO 2006/130982 A1 | 12/2006 |
| WO | WO 2007/003028 A1 | 1/2007 |
| WO | WO 2007/005910 A2 | 1/2007 |
| WO | WO 2007/005910 A3 | 1/2007 |
| WO | WO 2007/007208 A2 | 1/2007 |
| WO | WO 2007/012165 A1 | 2/2007 |
| WO | WO 2007/016677 A2 | 2/2007 |
| WO | WO 2007/016677 A3 | 2/2007 |
| WO | WO 2007/023005 A1 | 3/2007 |
| WO | WO 2007/023396 A2 | 3/2007 |
| WO | WO 2007/024501 A2 | 3/2007 |
| WO | WO 2007/024501 A3 | 3/2007 |
| WO | WO 2007/027859 A1 | 3/2007 |
| WO | WO 2007/028657 A1 | 3/2007 |
| WO | WO 2007/030266 A2 | 3/2007 |
| WO | WO 2007/030266 A3 | 3/2007 |
| WO | WO 2007/050379 A2 | 5/2007 |
| WO | WO 2007/050379 A3 | 5/2007 |
| WO | WO 2007/053292 A2 | 5/2007 |
| WO | WO 2007/053578 A2 | 5/2007 |
| WO | WO 2007/053578 A3 | 5/2007 |
| WO | WO 2007/054373 A1 | 5/2007 |
| WO | WO 2007/054818 A2 | 5/2007 |
| WO | WO 2007/057763 A2 | 5/2007 |
| WO | WO 2007/057763 A3 | 5/2007 |
| WO | WO 2007/059311 A2 | 5/2007 |
| WO | WO 2007/059311 A3 | 5/2007 |
| WO | WO 2007/064895 A2 | 6/2007 |
| WO | WO 2007/064895 A3 | 6/2007 |
| WO | WO 2007/067477 A1 | 6/2007 |
| WO | WO 2007/084533 A2 | 7/2007 |
| WO | WO 2007/084533 A3 | 7/2007 |
| WO | WO 2007/086884 A2 | 8/2007 |
| WO | WO 2007/086884 A3 | 8/2007 |
| WO | WO 2007/088050 A2 | 8/2007 |
| WO | WO 2007/088050 A3 | 8/2007 |
| WO | WO 2007/088123 A2 | 8/2007 |
| WO | WO 2007/088123 A3 | 8/2007 |
| WO | WO 2007/092284 A2 | 8/2007 |
| WO | WO 2007/092284 A3 | 8/2007 |
| WO | WO 2007/100910 A2 | 9/2007 |
| WO | WO 2007/100910 A3 | 9/2007 |
| WO | WO 2007/103190 A2 | 9/2007 |
| WO | WO 2007/103190 A3 | 9/2007 |
| WO | WO 2007/127725 A2 | 11/2007 |
| WO | WO 2007/127725 A3 | 11/2007 |
| WO | WO 2007/133922 A2 | 11/2007 |
| WO | WO 2007/133922 A3 | 11/2007 |
| WO | WO 2007/143185 A2 | 12/2007 |
| WO | WO 2007/143185 A3 | 12/2007 |
| WO | WO 2007/149437 A1 | 12/2007 |
| WO | WO 2007/149520 A2 | 12/2007 |
| WO | WO 2007/149520 A3 | 12/2007 |
| WO | WO 2008/005313 A2 | 1/2008 |
| WO | WO 2008/005313 A3 | 1/2008 |
| WO | WO 2008/013633 A2 | 1/2008 |
| WO | WO 2008/013633 A3 | 1/2008 |
| WO | WO 2008/020218 A1 | 2/2008 |
| WO | WO 2008/027203 A2 | 3/2008 |
| WO | WO 2008/027203 A3 | 3/2008 |
| WO | WO 2008/032212 A2 | 3/2008 |
| WO | WO 2008/038140 A2 | 4/2008 |
| WO | WO 2008/038147 A2 | 4/2008 |
| WO | WO 2008/062160 A1 | 5/2008 |
| WO | WO 2008/071242 A1 | 6/2008 |
| WO | WO 2008/088507 A2 | 7/2008 |
| WO | WO 2008/088507 A3 | 7/2008 |
| WO | WO 2008/095841 A2 | 8/2008 |
| WO | WO 2008/095841 A3 | 8/2008 |
| WO | WO 2008/098192 A2 | 8/2008 |
| WO | WO 2008/098192 A3 | 8/2008 |
| WO | WO 2008/100591 A2 | 8/2008 |
| WO | WO 2008/100591 A3 | 8/2008 |
| WO | WO 2008/110872 A2 | 9/2008 |
| WO | WO 2008/112391 A2 | 9/2008 |
| WO | WO 2008/112391 A3 | 9/2008 |
| WO | WO 2008/116497 A1 | 10/2008 |
| WO | WO 2008/116925 A1 | 10/2008 |
| WO | WO 2008/130567 A1 | 10/2008 |
| WO | WO 2008/141416 A1 | 11/2008 |
| WO | WO 2008/150505 A1 | 12/2008 |
| WO | WO 2008/152444 A2 | 12/2008 |
| WO | WO 2008/157393 A1 | 12/2008 |
| WO | WO 2009/007785 A2 | 1/2009 |
| WO | WO 2009/014616 A1 | 1/2009 |
| WO | WO 2009/014829 A2 | 1/2009 |
| WO | WO 2009/014829 A3 | 1/2009 |
| WO | WO 2009/019498 A2 | 2/2009 |
| WO | WO 2009/019498 A3 | 2/2009 |
| WO | WO 2009/019499 A2 | 2/2009 |
| WO | WO 2009/026680 A1 | 3/2009 |
| WO | WO 2009/036571 A1 | 3/2009 |
| WO | WO 2009/049208 A1 | 4/2009 |
| WO | WO 2009049208 A1 * | 4/2009 |
| WO | WO 2009/056991 A2 | 5/2009 |
| WO | WO 2009/064861 A2 | 5/2009 |
| WO | WO 2009/064861 A3 | 5/2009 |
| WO | WO 2009/072007 A2 | 6/2009 |
| WO | WO 2009/073643 A2 | 6/2009 |
| WO | WO 2009/073643 A3 | 6/2009 |
| WO | WO 2009/073940 A2 | 6/2009 |
| WO | WO 2009/073940 A3 | 6/2009 |
| WO | WO 2009/080795 A1 | 7/2009 |
| WO | WO 2009/086470 A2 | 7/2009 |
| WO | WO 2009/086470 A3 | 7/2009 |
| WO | WO 2009/087578 A2 | 7/2009 |
| WO | WO 2009/088433 A1 | 7/2009 |
| WO | WO 2009/090495 A2 | 7/2009 |
| WO | WO 2009/098113 A1 | 8/2009 |
| WO | WO 2009/098595 A2 | 8/2009 |
| WO | WO 2009/117182 A2 | 9/2009 |
| WO | WO 2009/117182 A3 | 9/2009 |
| WO | WO 2009/117183 A1 | 9/2009 |
| WO | WO 2009/124379 A1 | 10/2009 |
| WO | WO 2009/131931 A1 | 10/2009 |
| WO | WO 2009/155689 A1 | 12/2009 |
| WO | WO 2009/155690 A1 | 12/2009 |
| WO | WO 2010/002450 A2 | 1/2010 |
| WO | WO 2010/002450 A3 | 1/2010 |
| WO | WO 2010/033242 A2 | 3/2010 |
| WO | WO 2010/033242 A3 | 3/2010 |
| WO | WO 2010/045415 A2 | 4/2010 |
| WO | WO 2010/045465 A1 | 4/2010 |
| WO | WO 2010/048724 A1 | 5/2010 |
| WO | WO 2010/080213 A2 | 7/2010 |
| WO | WO 2010/080213 A3 | 7/2010 |
| WO | WO 2010/096320 A2 | 8/2010 |
| WO | WO 2010/096320 A3 | 8/2010 |
| WO | WO 2010/114669 A1 | 10/2010 |
| WO | WO 2010/120414 A2 | 10/2010 |
| WO | WO 2010/151505 A1 | 12/2010 |
| WO | WO 2011/005846 A1 | 1/2011 |
| WO | WO 2011/022680 A2 | 2/2011 |
| WO | WO 2011/061519 A2 | 5/2011 |
| WO | WO 2012/153331 A2 | 11/2012 |
| WO | WO 2013/006608 A1 | 1/2013 |
| WO | WO 2013/138073 A1 | 9/2013 |
| WO | WO 2013/138075 A1 | 9/2013 |

OTHER PUBLICATIONS

Brennan et al., "The Role of Nitric Oxide in Oral Diseases", *Archives of Oral Biology*, 2003, vol. 48, pp. 93-100.

Coban, A., et al., "The Effect of Nitric Oxide Combined with Fluoroquinolones against *Salmonellaenterica* Serovar Typhimurium in Vitro," *Mem Inst Oswaldo Cruz*, Rio de Janeiro, 2003, vol. 98(3), pp. 419-423.

Gupta, R., et al., "Bioactive materials for biomedical applications using sol-gel technology," *Biomed Mater.*, 2008, vol. 3, pp. 1-15.

Hetrick et al., "Bactericidal Efficacy of Nitric Oxide-Releasing Silica Nanoparticles," *Acsnano*, 2008, vol. 2(2), pp. 235-246.

(56) References Cited

OTHER PUBLICATIONS

Hrabie et al., "Chemistry of the nitric oxide-releasing diazeniumdiolate ("nitrosohydroxylamine") functional group and its oxygen-substituted derivatives," Chem Rev. 2002, 102, p. 1135-1154.
International Search Report and Written Opinion for corresponding PCT application No. PCT/US2009/005643, Date of Mailing May 24, 2010.
Iwakir, N. et al., Synthesis of Amphiphillic polysiloxanes and their properties for formation of nano-aggregates, Colloid Polym Sci, 2009; 287: 577-582.
Living Water Acid-Alkaline Balance http://www.livingwaterhealthsolutions.com/Articles/alkalize.php Accessed online Nov. 3, 2011.
McElhaney-Feser, G., et al., "Synergy of Nitric Oxide and Azoles against Candida Species in Vitro," Antimicrobial Agents and Chemotherapy, 1998, vol. 42(9), pp. 2342-2346.
Notification of the Transmittal of International Preliminary Report of Patentability for corresponding PCT Application No. PCT/US2009/005643, mailed Apr. 28, 2011.
Notification of the Transmittal of the International Search Report and the Written Opinion of the International Searching Authority, or the Declaration; International Search Report; Written Opinion of the International Search authority corresponding to PCT/US2010/046209; mailed May 23, 2011; 13 pages.
Notification of the Transmittal of the International Search Report and the Written Opinion of the International Searching Authority, or the Declaration; International Search Report; Written Opinion of the International Searching Authority corresponding to PCT/US2010/052460; Mailed Jan. 24, 2011; 10 pages.
Robson, MC, "Wound Infection. A Failure of Wound Healing Caused by an Imbalance of Bacteria," Surg Clin North Amer, Jun. 1997; 77(3): 637-50.
Saaral, NY, "The Equilibrium Between Endothelin-1/Nitric Oxide in Acne Vulgaris," Istanbul Tip Fakultesi Dergisi Cilt, 2008, 71(4).
Salivary pH Testing https://allicincenter.com/pdf/ph_testing.pdf Accessed online Nov. 3, 2011.
Sato, EF et al., J. Clin. Biochem. Nutr. (Pub Online Dec. 28, 2007), 42; pp. 8-13.
Schaffer, MR, et al., "Diabetes-impaired healing and reduced wound nitric oxide synthesis: a possible pathophysiologic correlation". Surgery, May 1997; 121(5):513-9.
Shi, HP, et al., "The role of iNOS in wound healing". Surgery, vol. 130, Issue 2, Aug. 2001; pp. 225-229.
Slowing, I.I., et al. Adv. Drug Del. Rev.(Aug. 2008), 60; pp. 1278-1288.
Stasko, N., et al., "Dendrimers as a Scaffold for Nitric Oxide Release," J. Am Chem. Soc., 2006, vol. 128, pp. 8265-8271.
Summersgill, J., et al., "Killing of Legionella pneumophila by nitric oxide in γ-interferon-activated macrophages," Journal of Leukocyte Biology, 1992, vol. 52, p. 625-629.
Tang, X., et al., "Synthesis of Beta-Lactamase Activated Nitric Oxide Donors," Biorgania & Medicinal Chemistry Letters, 2003, vol. 13, pp. 1687-1690.
Zhu, D., et al., "Corrosion protection of metals by water-based silane mixtures of bis-[trimethosysilylpropyl]amine and vinyltriacetoxysilane," Progress in Organic Coatings, 2004, vol. 49, pp. 42-53.
Coban, A., et al., "The Effect of Nitric Oxide Combined with Fluoroquinolones against Sahnonellaenterica Serovar Typhimurium in Vitro," Mem Inst Oswaldo Cruz, Rio de Janeiro, 2003, vol. 98(3), pp. 419-423.
Notification Concerning Transmittal of International Preliminary Report on Patentability for corresponding PCT Application No. PCT/US2009/005643, mailed Apr. 28, 2011.
Slowing, I.I., et al. Adv. Drug Del. Rev. (Aug. 2008), 60; pp. 1278-1288.
Stasko, N., et al., "Dendrimers as a Scaffold for Nitric Oxide Release," J. Am. Chem Soc., 2006, vol. 128, pp. 8265-8271.
Notification Concerning Transmittal of International Preliminary Report on Patentability (Chapter 1 of the Patent Cooperation Treaty) corresponding to PCT/US2010/046173; mailed Mar. 1, 2012.
Barbe et al. "Silica Particles: A Novel Drug-Delivery System", Advanced Materials, 2004, vol. 16(21), pp. 1959-1965.
Dobmeier, K. et al. "Antibacterial Properties of Nitric Oxide-Releasing Sol-Gel Microarrays", Biomacromolecules, 2004, vol. 5(6), pp. 2493-2495.
Farias-Eisner et al. "The Chemistry and Tumoricidal Activity of Nitric Oxide/Hydrogen Peroxide and the Implications to Cell Resistance/Susceptibility", The Journal of Biological Chemistry, 1996, vol. 271(11), pp. 6144-6151.
Hatton, H. et al. "Past, Present, and Future of Periodic Mesoporous Organosilicas the PMOs", Accounts of Chemical Research, vol. 38, No. 4, Apr. 2005, pp. 305-312.
Hetrick, E. et al. "Antibacterial Nitric Oxide-Releasing Xerogels: Cell Viability and Parallel Plate Flow Cell Adhesion Studies", Biomaterials, 2007, vol. 28(11) pp. 1948-1956.
Hetrick, E. et al. "Reducing Implant-Related Infections: Active Release Strategies", Chem. Soc. Rev., 2006, vol. 35, pp. 780-789.
Jones et al. "Antimicrobial properties of nitric oxide and its application in antimicrobial formulations and medical devices", Appl Microbiol Biotechnol, 88:401-407, 2010.
Lin, Hong-Ping et al. "Structural and Morphological Control of Cationic Surfactant-Templated Mesoporous Silica", Accounts of Chemical Research, vol. 35, No. 11, Nov. 2002, pp. 927-935.
Marxer, S. et al. "Sol-gel derived nitric oxide-releasing oxygen sensors", The Analyst, 2005, vol. 130(2), pp. 206-212.
Nablo, B. et al. "Inhibition of Implant-Associated Infections via Nitric Oxide Release", Biomaterials, 2005, vol. 26(34), pp. 6984-6990.
Nablo, B. et al. "Nitric oxide-releasing sol-gels as antibacterial coating for orthopedic implants", Biomaterials, 2005, vol. 26(8), pp. 917-924.
Pulfer, S. et al. "Incorporation of nitric oxide-releasing crosslinked polyethyleneimine microspheres into vascular grafts", J. Biomed Mater Res, 1997, vol. 37(2),pp. 182-189.
Reynolds, M. et al. "Nitric Oxide-Releasing Hydrophobic Polymers: Preparation, Characterization, and Potential Biomedical Applications", Free Radical Biology & Medicine, 2004, vol. 37(7), pp. 926-936.
Rothrock et al. "Synthesis of Nitric Oxide-Releasing Gold Nanoparticles", Journal of the American Chemical Society, vol. 127, No. 26, Jul. 2005, 9362-9363.
Shin, J. et al. "Nitric Oxide-Releasing Sol-Gel Particle/Polyurethane Glucose Biosensors", Anal Chem, 2004, vol. 76, pp. 4543-4549.
Stein A. et al. "Hybrid Inorganic Organic Mesoporous Silicates Nanoscopic Reactors Coming of Age", Advanced Materials, Oct. 2000, 1403-1419.
Zhu et al. "Effects on Nitric Oxide on Skin Burn Wound Healing", Journal of Burn Care & Research, vol. 29, No. 5, Sep./Oct. 2008, 804-814.
Zhu et al. "Nitric Oxide Accelerates the Recovery from Burn Wounds", World Journal of Surgery, 31: 624-631, 2007.
First Office Action corresponding to Chinese Application No. 201080047713.3 issued Feb. 28, 2013.
Zhang et al. "Nitric oxide releasing fumed silica particles: Synthesis, characterization, and biomedical application", Journal of American Chemical Society, 125, pp. 5015-5024, 2003.
Shin et al. "Synthesis of Nitric Oxide-releasing Silica Nanoparticles", Journal of American Chemical Society, 129, pp. 4612-4619, 2007.
Ashutosh et al. "Use of nitric oxide inhalation in chronic obstructive pulmonary disease" Thorax 55:109-113 (2000).
Azizzadeh et al. "Nitric Oxide Improves Cisplatin Cytotoxicity in Head and Neck Squamous Cell Carcinoma" Laryngoscope 111:1896-1900 (2001).
Barst et al. "Clinical perspectives with long-term pulsed inhaled nitric oxide for the treatment of pulmonary arterial hypertension" Pulmonary Circulation 2(2):139-147 (2012).
Benz et al. "Effect of Nitric Oxide in Ischemia/Reperfusion of the Pancreas" Journal of Surgical Research 106:46-53 (2002).

(56) References Cited

OTHER PUBLICATIONS

Bian et al. "Vascular System: Role of Nitric Oxide in Cardiovascular Diseases" *The Journal of Clinical Hypertension* 10(4):304-310 (2008).
Bloch et al. "Inhaled NO as a therapeutic agent" *Cardiovascular Research* 75:339-348 (2007).
Bonavida et al. "Therapeutic potential of nitric oxide in cancer" *Drug Resistance Updates* 9:157-173 (2006).
Bonavida et al. "Novel therapeutic applications of nitric oxide donors in cancer: Roles in chemo- and immunosensitization to apoptosis and inhibition of metastases" *Nitric Oxide* 19:152-157 (2008).
Boykin et al. "Hyperbaric Oxygen Therapy Mediates Increased Nitric Oxide Production Associated With Wound Healing: A Preliminary Study" *Advances in Skin & Wound Care* 20(7):382-388 (2007).
Boykin, Joseph, "Wound Nitric Oxide Bioactivity: A Promising Diagnostic Indicator for Diabetic Foot Ulcer Management" *Journal of Wound, Ostomy & Continence Nursing* 37(1):25-32 (2010).
Bruch-Gerharz et al. "Nitric Oxide in Human Skin: Current Status and Future Prospects" *The Journal of Investigative Dermatology* 110(1):1-7 (1998).
Cals-Grierson et al. "Nitric oxide function in the skin" *Nitric Oxide* 10:179-193 (2004).
Carlsson et al. "Intravesical Nitric Oxide Delivery for Prevention of Catheter-Associated Urinary Tract Infections" *Antimicrobial Agents and Chemotherapy* 49(6):2352-2355 (2005).
Davies et al. "Chemistry of the Diazeniumdiolates. 2. Kinetics and Mechanism of Dissociation to Nitric Oxide in Aqueous Solution" *Journal of the American Chemical Society* 123(23):5473-5481 (2001).
De Groote et al. "NO Inhibitions: Antimicrobial Properties of Nitric Oxide" *Clinical Infectious Diseases* 21(Suppl 2):S162-S165 (1995).
Fang, Ferric C. "Mechanisms of Nitric Oxide-related Antimicrobial Activity" *Journal of Clinical Investigation* 99(12):2818-2825 (1997).
Frederiksen et al. "Chemosensitization of Cancer in vitro and in vivo by Nitric Oxide Signaling" *Clinical Cancer Research* 13:2199-2206 (2007).
Ghaffari et al. "Potential application of gaseous nitric oxide as a topical antimicrobial agent" *Nitric Oxide* 14:21-29 (2006).
Herman et al. "Therapeutic potential of nitric oxide donors in the prevention and treatment of atherosclerosis" *European Heart Journal* 26:1945-1955 (2005).
Hirst et al. "Targeting nitric oxide for cancer therapy" *Journal of Pharmacy and Pharmacology* 59:3-13 (2006).
Howlin et al. "Nitric oxide-mediated dispersal and enhanced antibiotic sensitivity in *Pseudomonas aeruginosa* biofilms from the cystic fibrosis lung" *Archives of Disease in Childhood* 96:A45 (2011).
Huerta et al. "Nitric oxide donors: Novel cancer therapeutics (Review)" *International Journal of Oncology* 33:909-927 (2008).
Johnson et al. "Reduced ischemia/reperfusion injury via glutathione-initiated nitric oxide-releasing dendrimers" *Nitric Oxide* (2009) (7 pages).
Kiziltepe et al. "JS-K, a GST-activated nitric oxide generator, induces DNA double-strand breaks, activates DNA damage response pathways, and induces apoptosis in vitro and in vivo in human multiple myeloma cells" *Blood* 110(2):709-718 (2007).
Lamas et al. "Nitric oxide signaling comes of age: 20 years and thriving" *Cardiovascular Research* 75:207-209 (2007).
Liu et al. "Nitric Oxide Inhalation Improves Microvascular Flow and Decreases Infarction Size After Myocardial Ischemia and Reperfusion" *Journal of the American College of Cardiology* 50(8):808-817 (2007).
Luo et al. "Nitric oxide: a newly discovered function on wound healing" *Acta Pharmacologica Sinica* 26(3):259-264 (2005).
McGrowder et al. "Therapeutic Uses of Nitric Oxide-donating Drugs in the Treatment of Cardiovascular Diseases" *International Journal of Pharmacology* 2(4):366-373 (2006).

Napoli et al. "Nitric oxide and atherosclerosis: An update" *Nitric Oxide* 15:265-279 (2006).
Phillips et al. "Nitric Oxide Mechanism of Protection in Ischemia and Reperfusion Injury" *Journal of Investigative Surgery* 22:46-55 (2009).
Saavedra et al. "Esterase-Sensitive Nitric Oxide Donors of the Diazeniumdiolate Family: in Vitro Antileukemic Activity" *Journal of Medicinal Chemistry* 43(2):261-269 (2000).
Schairer et al. "The potential of nitric oxide releasing therapies as antimicrobial agents" *Virulence* 3(3):271-279 (2012).
Schulz et al. "Nitric oxide in myocardial ischemia/reperfusion injury" *Cardiovascular Research* 61:402-413 (2004).
Schwentker et al. "Nitric oxide and wound repair: role of cytokines?" *Nitric Oxide* 7:1-10 (2002).
Simeone et al. "N-(4-Hydroxyphenyl)retinamide and nitric oxide pro-drugs exhibit apoptotic and anti-invasive effects against bone metastatic breast cancer cells" *Carcinogenesis* 27(3):568-577 (2006).
Siriussawakul et al. "Role of nitric oxide in hepatic ischemia-reperfusion injury" *World Journal of Gastroenterology* 16(48):6079-6086 (2010).
Stevens et al. "Nitric Oxide-Releasing Silica Nanoparticle Inhibition of Ovarian Cancer Cell Growth" *Molecular Pharmaceuticals* 7(3):775-785 (2010).
Terpolilli et al. "Inhalation of Nitric Oxide Prevents Ischemic Brain Damage in Experimental Stroke by Selective Dilatation of Collateral Arterioles" *Circulation Research* 110:727-738 (2012).
Thomas et al. "Hypoxic inducible factor 1α, extracellular signal-regulated kinase, and p53 are regulated kinase, and p53 are regulated by distinct threshold concentrations of nitric oxide" *PNAS* 101(24):8894-8899 (2004).
Weller, Richard "Nitric oxide donors and the skin: useful therapeutic agents?" *Clinical Science* 105:533-535 (2003).
Wink et al. "The multifaceted roles of nitric oxide in cancer" *Carcinogenesis* 19(5):711-721 (1998).
Witte et al. "Nitric oxide enhances experimental wound healing in diabetes" *British Journal of Surgery* 89:1594-1601 (2002).
Witte et al. "Role of nitric oxide in wound repair" *The American Journal of Surgery* 183:406-412 (2002).
Yetik-Anacak et al. "Nitric oxide and the endothelium: History and impact on cardiovascular disease" *Vascular Pharmacology* 45:268-276 (2006).
Chinese Office Action Corresponding to Chinese Patent Application No. 201080047713.3; Date of Mailing: May 27, 2014.
Notification of Transmittal of the International Search Report and the Written Opinion of the International Searching Authority, or the Declaration corresponding to PCT/US2012/45390 mailed Dec. 11, 2012.
Notification of Transmittal of the International Search Report and the Written Opinion of the International Searching Authority, or the Declaration corresponding to International Application No. PCT/US2011/065043 mailed Apr. 24, 2012.
Boykin et al. "HBO Mediates Increased Nitric Oxide Production Associated With Wound Healing" *Wound Repaid and Regeneration* 12(2):A15 (Abstract 054) (2004).
Amadeu et al. "Nitric Oxide Donor Improves Healing if Applied on Inflammatory and Proliferative Disease", *J. Surgical Research* 149:84-93 (2008).
Bohl Masters et al. "Effects of nitric oxide releasing vinyl poly(vinyl alcohol) hydrogel dressings on dermal wound healing in diabetic mice", *Wound Repair and Regeneration* 10(5):286-294 (2002).
Hetrick et al. "Anti-biofilm efficacy of nitric oxide-releasing silica nanoparticles", *Biomaterials* 30:2782-2789 (2009).
Notification of Transmittal of the International Search Report and the Written Opinion of the International Searching Authority, or the Declaration corresponding to International Application No. PCT/US2010/046173 mailed Dec. 6, 2010.

* cited by examiner

TOPICAL GELS AND METHODS OF USING THE SAME

CROSS-REFERENCE TO RELATED APPLICATIONS

The present application is a 35 U.S.C. §371 national phase application of PCT International Application No. PCT/US2010/046173, having an international filing date of Aug. 20, 2010, claiming priority to U.S. Provisional Application Ser. No. 61/235,933, filed Aug. 21, 2009. The disclosures of each application are incorporated herein by reference in their entireties. The above PCT International Application was published in the English language and has been accorded International Publication No. WO 2011/022652 A1.

FIELD OF THE INVENTION

The present invention relates to topical gels that may controllably release nitric oxide. The present invention also relates to methods of using topical gels that may controllably release nitric oxide.

BACKGROUND OF THE INVENTION

Skin has a myriad of functions, including protection against pathogens and excessive water loss, insulation, temperature regulation, sensation and protection of vitamin B folates. As such, impairment or ailments of the skin may significantly affect the health of a person or animal. Furthermore, such impairments or ailments may cause irritation, pain or other discomfort and may undesirably affect the person or animal's physical appearance.

An important aspect for the treatment of many skin impairments or ailments, including wounds and burns, is the control of infection, which may facilitate the healing process. Topical medicaments are commonly used tools to protect wounds and other skin ailments from infection. Antimicrobial agents are often incorporated into topical medicaments and wound dressing to treat and prevent infection. However, there may be disadvantages associated with use of antimicrobial agents. It has been observed that an increasing number of pathogens have developed resistance to conventional antibiotic treatments. According to statistics, antibiotic-resistant pathogens are the primary reason for a majority of all lethal nosocomial infections. See Robson et al., Surg. Clin. N. Am. 77, 637-650 (1977). Furthermore, many antimicrobial agents not only kill pathogens, but also impose a threat to the proliferating granulation tissue, fibroblasts and keratinocytes that may help with the wound healing process. Additionally, some antimicrobial agents may cause allergic reactions in some patients.

It is known that nitric oxide possesses a broad-spectrum of antimicrobial activity and may be used as an alternative to conventional antibiotics for drug resistant bacteria. Furthermore, some recent studies have demonstrated that nitric oxide may also play an important role in the wound healing process by promoting angiogenesis through stimulation of vascular endothelial growth factor (VEGF) and increase fibroblast collagen synthesis. See Schaffer M R, et al., *Diabetes-impaired healing and reduced wound nitric oxide synthesis: A possible pathophysiologic correlation.* Surgery 1997; 121(5):513-9; and Shi H P, et al., *The role of iNOS in wound healing.* Surgery 2001; 130 (2):225-9. Thus, nitric oxide presents a promising addition and/or alternative to the conventional antibiotic treatments. Furthermore, nitric oxide has been shown to have other beneficial properties, including reducing inflammation and participation in wound healing biochemical cascades. Unfortunately, the relationship between exogenously applied concentrations of nitric to promote healing, mediate inflammation, or treat infection are not clearly understood.

Nitric oxide is a gas at ambient temperature and atmospheric pressure, and it has a short half-life in a physiological milieu. Several small molecule nitric oxide donor prodrugs have been developed which have contributed greatly to the understanding of nitric oxide in a number of disease states. However, due to their issues with stability, indiscriminate NO-release, monotypical nitric oxide release kinetics, and inability to target specific tissue types, optimal solutions for administering nitric oxide outside of its gaseous form have not yet been achieved. Reproducibly delivering the correct levels of nitric oxide for a given therapeutic indication is critical because the release of large amounts of nitric oxide may be toxic or create undesirable side effects such as an increase in inflammation. Therefore, it has been challenging to use nitric oxide for topical therapeutic applications, particularly for reproducibly delivering nitric oxide in a controlled manner from vehicles capable of targeting tissue structures.

As an example, previous investigators have explored the use of topical formulations containing an alkali nitrite source in combination with ascorbic acid or other organic acid, that upon admixture or mixing create a rapid bolus of nitric oxide release. While the antimicrobial efficacy of nitric oxide released via this approach has been shown, it may also result in decrease in angiogenesis, increase in inflammation and unwanted toxicity. Thus, the need exists for topical treatments and medicaments that can release nitric oxide by a controlled delivery method.

SUMMARY OF THE INVENTION

Provided according to embodiments of the invention are topical gels that release nitric oxide (NO). In some embodiments of the invention, the topical gels include diazeniumdiolate-functionalized polysiloxane macromolecules and a hydrophobic, non-aqueous gel base. In some embodiments, the hydrophobic, non-aqueous gel base is a silicone gel. Furthermore, in some embodiments, the diazeniumdiolate-functionalized polysiloxane macromolecules and gel excipients have an octanol/water partition coefficient in a range of 0.1 to 7.

In some embodiments of the invention, the topical gels include diazeniumdiolate-functionalized polysiloxane macromolecules and a hydrophilic gel base. As such, in some embodiments, the diazeniumdiolate-functionalized polysiloxane macromolecules and the gel excipients have an octanol/water partition coefficient in a range of −2 to 0.

In some embodiments of the invention, the concentration of the diazeniumdiolate-functionalized polysiloxane macromolecules in the gel is in a range of 0.1 to 20 weight %.

In some embodiments of the invention, the diazeniumdiolate-functionalized polysiloxane macromolecules have a hydrodynamic radius in a range of 1000 nm to 10 microns. In some embodiments of the invention, the diazeniumdiolate-functionalized polysiloxane macromolecules have a hydrodynamic radius in a range of 1 nm to 100 nm.

The nitric oxide storage of the gels may be tailored. In some embodiments, the nitric oxide storage per gram is in a range of 0.1 pmol NO/g to 100 nmol/g gel. In some embodiments, the nitric oxide storage per gram is in a range of 1 nmol NO/g to 10 µmol/g gel. In some embodiments, the nitric oxide storage per gram is in a range of 10 µmol NO/g to 1 mmol/g gel.

In some embodiments of the invention, the gels further include other therapeutic agents such as an anti-acne agent, antimicrobial agent, benzoyl peroxide, or a corticosteroid.

Also provided herein are methods of treating wounds that include wound comprising applying the topical gel according to an embodiment of the invention. In particular embodiments, methods include treatment of burns and treatment of acne.

BRIEF DESCRIPTION OF THE DRAWINGS

The accompanying drawings, which are included to provide a further understanding of the invention and are incorporated in and constitute a part of this application, illustrate certain embodiment(s) of the invention.

DETAILED DESCRIPTION OF EMBODIMENTS OF THE INVENTION

Figure 1:
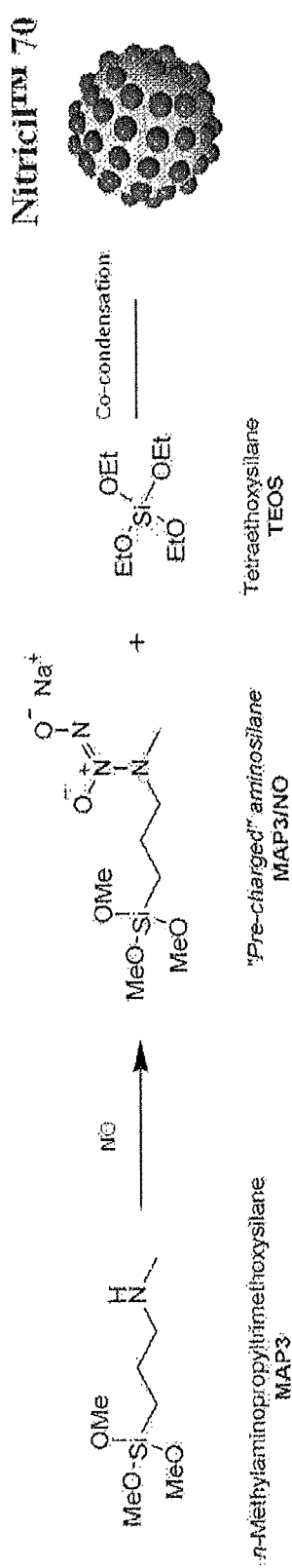
FIG. 1 is a schematic for the synthesis of diazeniumdiolate-functionalized polysiloxane macromolecules according to some embodiments of the invention.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Chemical Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR$^1$R'', wherein R$^1$ and R'' can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, f-butoxyl, and pentoxyl. The term "oxyalkyl" can be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e., respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as NR$_3$, NH$_3$, NHR$_2$, and NH$_2$R, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a cation stabilized diazeniumdiolate (i.e., NONO$^-$X$^+$).

The terms "cationic amine" and "quaternary amine" refer to an amino group having an additional (i.e., a fourth) group, for example a hydrogen or an alkyl group bonded to the nitrogen. Thus, cationic and quarternary amines carry a positive charge.

The term "alkylamine" refers to the -alkyl-NH$_2$ group.

The term "carbonyl" refers to the —(C=O)— group.

The term "carboxyl" refers to the —COOH group and the term "carboxylate" refers to an anion formed from a carboxyl group, i.e., —COO$^-$.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group. The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to $Si(OR)_4$, wherein R is alkyl. Each alkyl group can be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "silanol" refers to a Si—OH group.

Provided according to some embodiments of the invention are topical medicaments that include NO-releasing macromolecules. In some embodiments, the NO-releasing macromolecules are diazeniumdiolate-functionalized polysiloxane macromolecules. Furthermore, in some embodiments, the medicaments include diazeniumdiolate-functionalized polysiloxane macromolecules in a gel.

In some embodiments of the invention, the properties of the gel are selected based on the properties of the diazeniumdiolate-functionalized polysiloxane macromolecules and the indication for which the topical gel is to be used, such that the interaction of the properties of the gel, macromolecule and skin environment act to provide the desired NO release profile. At the same time, the gel must be suitably stable and resist decomposition prior to topical application.

The Diazeniumdiolate-Functionalized Polysiloxane Macromolecules

The term "diazeniumdiolate-functionalized polysiloxane macromolecules" refers co-condensed polysiloxane macromolecules functionalized with diazeniumdiolate, such as the NO-releasing particles described in U.S. Publication No. 2009/0214618, the disclosure of which is incorporated by reference herein in its entirety. Such particles may be prepared by methods described therein.

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method can be used to create co-condensed siloxane networks and materials more densely functionalized with NO-donors.

The co-condensed siloxane network can be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups can be the same or different. In some embodiments the tetraalkoxysilane is selected as tetramethyl orthosilicate (TMOS) or tetraethyl orthosilicate (TEOS). In some embodiments, the aminoalkoxysilane has the formula: R"—(NH—R')$_n$—Si(OR)$_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane can be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (amino ethylaminomethyl) phenethyltrimethoxysilane (AEMP3); [3-(methylamino) propyl]trimethoxysilane (MAP3); N-butylamino-propyltrimethoxysilane(n-BAP3); t-butylamino-propyltrimethoxysilane (t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: NH [R'—Si(OR)$_3$]$_2$, wherein R is alkyl and R' is alkylene. In some embodiments, the aminoalkoxysilane can be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R"—N(NONO$^-$X$^+$)—R'—Si(OR)$_3$, wherein R is alkyl or silyl, R' is alkylene or aralkylene, R" is alkyl or alkylamine, and X$^+$ is a cation selected from the group consisting of Na$^+$, K$^+$, Cs$^+$, Li$^+$, NH$_4^+$, or other quaternary ammonium cation.

In some embodiments of the invention, the diazeniumdiolate-functional aminoalkoxysilane may be O$^2$-protected prior to the preparation of the nitric oxide releasing macromolecules. Such O$^2$-protected diazeniumdiolate functional aminoalkoxysilanes may have the formula: R"—N(NONO—R''')—R'—Si(OR)$_3$, wherein each R is independently H, alkyl or substituted alkyl, R' is substituted or unsubstituted alkylene, substituted or unsubstituted arylene, substituted or unsubstituted alkylarylene or substituted or unsubstituted arylalkylene, R" is H, alkyl or substituted alkyl and R''' is a protecting group that imparts enzymatic, photolytic, or thiolation triggering mechanisms. Such protecting groups are known to those skilled in the art of forming O$^2$-protected diazeniumdiolates.

The chemical composition of the siloxane network, (e.g., amount or the chemical composition of the aminoalkoxysilane), the porosity of the silica network within the macromolecular structure, the size of the co-condensed silica particles, and the nitric oxide charging conditions (e.g., the solvent and base) can be varied to optimize the amount and duration of nitric oxide release. Thus, in some embodiments, the composition of the silica particles can be modified to regulate the half-life of NO release from silica particles with half-lives of nitric oxide release ranging from slow, defined by $t_{1/2}$ values greater than 60 minutes to fast, defined by $t_{1/2}$ values ranging from 30 seconds to 10 minutes.

In some embodiments of the invention, the co-condensed siloxane network of nitric oxide releasing silica particles is formed from at least one additional silane that modifies surface charge and/or hydrophilicity/hydrophobicity of the co-condensed silica product which affect the octanol/water partition coefficient of the macromolecular delivery vehicle. These parameters control the route of skin penetration, depth of penetration, and diffusion of the diazeniumdiolate-modified polysiloxane macromolecules out of topical gel vehicles. Any suitable alkoxysilane that may impart surface charge to the diazeniumdiolate-modified polysiloxane macromolecule may be used. Thus, in some embodiments, the additional alkoxysilane may include a cationic alkoxysilane such as (2-N-benyzlaminoethyl)-3-aminopropyl-trimethoxysilane, hydrocholoride; bis(methoxyethyl)-3-trimethoxysilylpropyl-ammonium chloride; N—N-didecyl-N-methyl-N-(3-trimethoxysilyl)ammonium chloride; N-trimethyoxysilylpropyl-N,N,N-trimethyl ammonium chloride; octadecylbis(triethoxysilylpropyl)-ammonium chloride; and octadecyldimethyl(3-trimethoxysilylpropyl) ammonium chloride. In some embodiments, the additional alkoxysilane may include an anionic alkoxysilanes such as 3-trihydroxysilylpropylmethyl phosphonate, sodium salt and carboxyethylsilanetriol, sodium salt.

Any suitable alkoxysilane that may impart hydrophilic properties to the diazeniumdiolate-modified polysiloxane macromolecule may be used. Alkoxysilanes containing repeat poly(ethylene)oxy groups may be used to increase the wetability of the NO-releasing particles thereby helping to improve biocompatibility upon topical application and also enhance the rate of water uptake into the co-condensed siloxane coating. Surface hydrophilicity can thus be utilized to enhance the NO-release kinetics of the diazeniumdiolated aminoalkoxysilane derivatives. Therefore, in some embodiments, the multifunctional alkoxysilane may include a hydrophilic silane such as N-triethoxysilylpropyl)-O-polyethyleneoxide urethane; N-3-[amino(polypropylenoxy)] aminopropyltrimethoxysilane; bis-[3-(triethoxysilylpropoxy)-2-hydroxypropoxy]polyethylene oxide; bis(3-triethoxysilylpropyl)polyethylene oxide (25-30); [hydroxy (polyethyleneoxy)propyl]-triethoxysilane; and 2-[methoxy (polyethyleneoxy)propyl]-trimethoxysilane.

Any suitable alkoxysilane that may impart hydrophobic properties to the diazeniumdiolate-modified polysiloxane macromolecule may be used. Hydrophobic silanes are known to those skilled in the art to increase lipophilicity of particle surfaces. In some embodiments, the additional alkoxysilane may include linear alkyl, branched and cyclic alkylalkoxysilanes having at least three carbon atoms, substituted and unsubstituted phenyl alkoxysilanes, and fluorinated alkoxysilanes. Exemplary fluoroalkoxysilanes may include heptadecafluoro-1,1,2-2-tetrahydrodecyl)triethoxysilane (shown in FIG. 2I), (3,3,3-trifluoropropyl)trimethoxysilane, (perfluoroalkyl)ethyltriethoxysilane, nonafluorohexyltrimethoxysilane, nonafluorohexyltriethoxysilane, (tridecafluoro-1,1,2,2-tetrahydrooctyl)triethoxysilane, and (tridecafluoro-1,1,2,2-tetrahydrooctyl)trimethoxysilane.

The hydrophilicity of the diazeniumdiolate-functionalized polysiloxane macromolecules can be assessed by the use of a water/octanol partition coefficient. See *Octanol-Water Partition Coefficients: Fundamentals and Physical Chemistry, Vol.* 2 *of Wiley Series in Solution Chemistry*. Chichester: John Wiley & Sons Ltd. (1997), which is herein incorporated by reference in its entirety. For example, hydrophobic diazeniumdiolate-functionalized polysiloxane macromolecules may have a water/octanol partition coefficient in a range of 0.1 to 7, and hydrophilic diazeniumdiolate-functionalized polysiloxane macromolecules may have a water/octanol partition coefficient in a range of −2 to 0.

In some embodiments of the invention, the hydrodynamic radius of the NO-releasing macromolecule is within a range of 1 nm to 100 nm, which may maximize trans-epidermal skin penetration and enhance nitric oxide delivery to deeper skin structures or, the size of the macromolecular scaffold may be selected to be in a range of 101 nm to 1000 nm to selectively accumulate diazeniumdiolate-modified polysiloxane macromolecules in the stratum corneum and limit skin penetration, systemic absorption, and any resulting toxicity of the macromolecular scaffold, or the size of the macromolecule scaffold may be selected to be in a range of 1000 nm to 10,000 nm to target skin penetration via the trans-follicular route. Selective delivery to the stratum corneum, epidermis or dermis may be achieved by varying the particle size. Skin naturally has a low permeability to particulate materials and the stratum corneum provides an effective barrier to most inorganic nanosized particles with gold nanoparticles, silver nanoparticles, quantum dots, titanium dioxodie, and zinc oxide being the most extensively studied. See, e.g., Baroli, B., Penetration of Nanoparticles and Nanomaterials in the Skin: Fiction or Reality? *Journal of Pharmaceutical Sciences,* 2009 December; 99:21-50. Despite the current understanding of one skilled in the art of skin penetration, the skin penetration of silica particles as a function of size is poorly understood.

The diazeniumdiolate-functionalized polysiloxane macromolecules may be present in medicaments according to embodiments of the invention at any suitable concentration, but in some embodiments, the diazeniumdiolate-functionalized polysiloxane macromolecules are present in the medicaments at a concentration sufficient to increase the rate of wound healing, decrease inflammation and/or exert an antimicrobial effect. In particular embodiments, the concentration of diazeniumdiolate-functionalized polysiloxane macromolecules is in a range of 0.01 percent to 20 percent w/w. In some embodiments, the concentration of the diazeniumdiolate-functionalized polysiloxane macromolecules in the medicament may be adjusted to modulate the amplitude of nitric oxide release (mol NO/g medicament) either by changing the weight percentage in the gel or by varying the loading of nitric oxide on the macromolecular scaffold to create a desirable therapeutic outcome.

In some embodiments, to prevent platelet activation and aggregation, the final NO storage per gram of gel may be in a range of 0.1 pmol NO/g gel to 100 nmol/g gel. In some embodiments, to reduce inflammation and associated inflammatory response factors, the final NO storage per gram of gel may be in a range of 100 pmol NO/g gel to 1 umol NO/g gel. In some embodiments, to promote wound healing, the final NO storage per gram of gel may be in a range of 1 nmol NO/g gel to 10 μmol NO/g gel. In some embodiments, to exert antimicrobial activity, the final NO storage per gram of gel may be in a range of 10 μmol NO/g gel to 1 mmol NO/g gel. In some embodiments, to treat biofilms by dispersal, the final NO storage per gram of gel may be in a range of 10 nmol NO/g gel to 1 μmol NO/g gel, and in some embodiments, to treat biofilms by direct microbicidal activity, the final NO storage per gram of gel may be in a range of 100 μmol NO/g gel to 1 mmol NO/g gel.

Topical Gels

The properties of the topical gels, including the NO-release profile, may be tailored by the selection of the gel composition. The gels may also provide beneficial or therapeutic action to the skin or wound bed (e.g., moisturize, absorb wound exudate, provide an occlusive barrier, etc.) that may directly affect skin conditions or wound healing. The excipients that form the gels may also indirectly affect wound healing by affecting the stability of the diazeniumdiolate-functionalized polysilane macromolecules or other therapeutic agents within the medicament and/or controlling the rates of decomposition of the NO donors to generate nitric oxide. The intrinsic pH of the topical gel can be elevated to between 8 and 10 to maintain NO donor stability and react with the acid mantle on the surface of the skin to neutralize pH and initiate decomposition of diazeniumdiolate nitric oxide donors.

Excipients for use in topical gels are well-known in the art and examples may be found in the *Handbook of Pharmaceutical Excipients* (Rowe, R. C. et al., APhA Publications; 5$^{th}$ ed., 2005). Exemplary excipients may include waxes, various sugars and types of starch, polymers, gels, emollients, thickening agents, rheology modifiers, humectants, glycerol, organic basic compounds, cellulose derivatives, gelatin, vegetable oils, polyethylene glycols and solvents. Examples of rheology modifiers include Carbopol, hydroxypropyl cellulose, $C_{26-28}$ alkyl dimethicone, $C_{26-28}$ alkyl methicone, polyphenylsisquioxane, trimethylsiloxysilicate, crosspolymers of cyclopentasiloxane and dimethicone/vinyltrimethylsiloxysilicate, fumed silica (e.g. Cab-O-Sil M5P), and mixtures thereof. Examples of emollients include glycerine, pentylene glycol, sodium pyrrolidone carboxylic acid, lanolin, saccharide isomerate, stearoxy dimethicone, stearyl dimethicone, and mixtures thereof. Emollients may be useful to prevent stratum corneum dehydration occurring due to the use of anhydrous solvents in the formulation. Examples of organic bases include 2-amino-2-methyl propanol, niacinamide, methanolamines, triethanolamines, Trisamino, AMP-95, AmP-Ultra PC 2000, triisopropanolamine, diisopropanolamine, Neutrol TE, Ethomeen, and mixtures thereof. The organic base may render the pH of the medicament basic or neutral, and may directly affect the release of NO from the diazeniumdiolate groups by slowing donor decomposition with increasing alkalinity.

Other exemplary excipients include water-soluble porogens. A water-soluble porogen is an additive that may facilitate water uptake and diffusion into the gel. Any suitable porogen may be used, but in some embodiments, the porogen may include sodium chloride, potassium chloride, sucrose, glucose, lactose, sorbitol, xylitol, polyethylene glycol, polyvinylpyrrollidone, polyvinyl alcohol or mixtures thereof. Electrolytes, like KCl, may also be added as excipients to enhance the stability of diazeniumdiolate NO donors.

Polymers may also act as excipients in topical gels. Exemplary polymers include hydrophilic polyurethanes, hydrophilic polyacrylates, co-polymers of carboxymethylcellulose and acrylic acid, N-vinylpyrrolidone, poly(hydroxy acids), polyanhydrides, polyorthoesters, polyamides, polycarbonates, polyalkylenes (e.g., polyethylene and polypropylene), polyalkylene glycols (e.g., poly(ethylene glycol)), polyalkylene oxides (e.g., polyethylene oxide), polyalkylene terephthalates (e.g., polyethylene terephthalate), polyvinyl alcohols, polyvinyl ethers, polylvinyl esters, polyvinyl halides (e.g., poly(vinyl chloride)), polyvinylpyrrolidone, polysiloxanes, polyvinyl acetates), polystyrenes, polyurethane copolymers, cellulose, derivatized celluloses, alginates, poly(acrylic acid), poly(acrylic acid) derivatives, acrylic acid copolymers, methacrylic acid, methacrylic acid derivatives, methacrylic acid copolymers, poly(butyric acid), poly(valeric acid), poly(lactide-co-caprolactone), copolymers thereof and blends thereof.

In some embodiments of the invention, the polymers may be superabsorbent polymers (SAPs). A polymer is considered superabsorbent, as defined per IUPAC, as a polymer that can absorb and retain extremely large amounts of water relative to its own mass. SAPs may absorb water up to 500 times their own weight and may swell up to 1000-times their original volume. Particular SAPs of interest include sodium polyacrylate, the polyurethane Tecophilic TG-2000, and polymers prepared by the use of polyacrylamide copolymer, ethylene maleic anhydride copolymer, cross-linked carboxymethyl-cellulose, polyvinyl alcohol copolymers, polyvinylpyrrolindone and cross-linked polyethylene oxide. In some embodiments, the SAP may absorb water from the wound bed, thereby causing NO to release from the diazeniumdiolate-functionalized polysilane macromolecules.

In some embodiments of the invention, polymers that are relatively hydrophobic may be used. Any suitable hydrophobic polymer may be used. However, exemplary polymers that are relatively hydrophobic include aromatic polyurethanes, silicone rubber, polysiloxanes, polycaprolactone, polycarbonate, polyvinylchloride, polyethylene, poly-L-lactide, poly-DL-glycolide, polyetheretherketone (PEEK), polyamide, polyimide and polyvinyl acetate. In addition, a hydrophobic gel-base and/or rheology modifier may be used.

In some embodiments of the invention, the polymers may act as thickening agents in the medicaments. Specifically, the polymeric portion of the gel may act as a visco-elastic substance and may retain the gel at the site of application, along with the diazeniumdiolate-functionalized polysilane macromolecules dispersed therein.

In some other embodiments, a gel that includes a polymer may have spreadability such that it forms a thin film when applied on the skin surface. This film may enable the application of the contained NO-releasing polysiloxane macromolecules over a wide area, and may serve to maintain the NO-releasing polysiloxane macromolecules on the affected area of the skin.

Other excipients may include various ionic or non-ionic compounds to maintain stability of the formulation, thereby protecting from the de-emulsification, settling, agglomeration or degradation of the formulation constituents that may reduce its therapeutic or aesthetic value.

Examples of ionic compounds may include salts such as sodium chloride, potassium chloride; cationic, anionic or zwitterionic surfactants such as sodium dodecyl sulfate (SDS), perfluorooctanoate (PFOA), perfluorooctanesulfonate (PFOS), ammonium lauryl sulfate (ALS), sodium lauryl ether sulfate (SLES), alkyl benzene sulfonate, cetyl trimethylammonium bromide (CTAB), cetylpyridinium chloride (CPC), polyethoxylated tallow amine (POEA), benzalkonium chloride (BAC), benzethonium chloride, dodecyl betaine, cocamidopropyl betaine and cocoamphoglycinate.

Examples of non-ionic compounds that may act as excipients include non-ionic surfactants such as Pluronic, Tween, AMP, and Brij family of surfactants; and surfactants derived from biological sources, e.g, natural or semi-synthetic surfactants, such as oleic acid, sorbitan trioleate, sorbitan monooleate, lecithin, cocamide MEA, cocamide DEA and cocamidopropyl betaine. Surfactants (both ionic and non-ionic) may reduce the interfacial surface energy and may facilitate spreading of the ointment or liquid over a wider area.

In some embodiments of the invention, solvent excipients may be used as a carrier vehicle for the NO-releasing macromolecules and other excipients. The polymer chains may interact with the solvent and undergo swelling to form a network that may impart visco-elastic properties to the medicament. In some embodiments of the medicament, the solvent may evaporate upon application, leaving a residual film of the polymer along with the entrapped NO-releasing macromolecules.

Exemplary solvent excipients that may be useful in hydrophilic formulations may include dimethyl isosorbide, propylene glycol, glycerol, isopropanol, ethanol, benzyl alcohol, ethylene glycol, polyethylene glycol, ethoxydiglycol or mixtures thereof. Exemplary solvent excipients that may be useful in hydrophobic formulations may include capric/caprylic triglycerides, isopropyl myristate, mineral oil, isododecane, isodecyl neopentanoate, butylene glycol, pentylene glycol, hexylene glycol, methoxypolyethyleneglycol, cyclopentasiloxane, cyclotetrasiloxane, dimethicone, caprylyl methicone or mixtures thereof. In some embodiments, the hydrophilic gel may be an alcoholic gel, wherein the gel has an alcohol content in a range of 20 to 90 weight percent, and in some cases, in a range of 60 to 85 weight percent.

In addition to the diazeniumdiolate-functionalized polysiloxane macromolecules and excipients, the topical gels may also include at least one additional therapeutic agent such as antimicrobial agents, anti-acne agents, anti-inflammatory agents, analgesic agents, anesthetic agents, antihistamine agents, antiseptic agents, immunosuppressants, anti-hemorrhagic agents, vasodilators, wound healing agents, anti-biofilm agents and mixtures thereof.

Examples of antimicrobial agents include penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimetliamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, Linezolid, Synercid, Aztreonam, and Metronidazole, Epiroprim, Sanfetrinem sodium, Biapenem, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil.

Examples of topical anti-acne agents include adapalene, azelaic acid, benzoyl peroxide, clindamycin and clindamycin phosphate, doxycycline, erythromycin, keratolytics such as salicylic acid and retinoic acid (Retin-A"), norgestimate, organic peroxides, retinoids such as isotretinoin and tretinoin, sulfacetamide sodium, and tazarotene. Particular anti-acne agents include adapalene, azelaic acid, benzoyl peroxide, clindamycin (e.g., clindamycin phosphate), doxycycline (e.g., doxycycline monohydrate), erythromycin, isotretinoin, norgestimate, sulfacetamide sodium, tazarotene, etretinate and acetretin.

Examples of antihistamine agents include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include nonsteroidal anti-inflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocalne; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include thrombin, phytonadione, protamine sulfate, aminocaproic acid, tranexamic acid, carbazochrome, carbaxochrome sodium sulfanate, rutin and hesperidin.

In addition to the diazeniumdiolate-functionalized polysiloxane macromolecules, excipients, and other therapeutic agents, the gels may also include other compounds that improve the organoleptic properties of the medicament. Examples of such compounds include perfumes, dyes and colorants; chelating agents including but not limited to EDTA, EGTA, CP94, citric acid; preservatives including but not limited to quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Tailoring Gels for Particular Therapeutic Uses

Wound healing occurs in several different phases, and may take place over 0-12 (or more) months. Wound healing phases include:
 (i) Clotting
 (ii) Cell Proliferation
 (iii) Granulation Tissue Formation
 (iv) Epithelialization
 (v) Neovascularization or angiogenesis
 (vi) Wound Contraction
 (vii) Matrix deposition including collagen synthesis
 (viii) Tissue Remodeling, including scar formation and scar remodeling Nitric oxide may play a role in wound healing by a number of different mechanisms. First, extended exposure to low concentrations of nitric oxide may promote wound healing whereby nitric oxide acts as a signaling molecule in a number of wound healing cascades. Additionally, nitric oxide may also play a role in mitigating inflammation following injury. Modulation of inflammatory cytokines and cells of the inflammatory response via nitric oxide may significantly alter the wound healing phases above. Additionally, wound complications and pain may be significantly reduced with topical administration of nitric oxide as an anti-inflammatory agent. Furthermore, nitric oxide may act as a broad spectrum antimicrobial agent, particularly at relatively high concentrations. The antimicrobial effects of nitric oxide are broad ranging and different wound types may be colonized with different wound pathogens (e.g., gram negative bacteria, gram positive bacteria, fungus, etc.). Additionally, some pathogens may be more sensitive to nitric oxide than other pathogens. In some embodiments, nitric oxide may act as an antimicrobial agent by directly killing planktonic bacteria and other organisms; directly killing biofilm embedded bacteria and other organisms; indirectly killing microorganisms through nitrosative/oxidative stress; loosening biofilm matrix; increasing drug permeability across microbial membranes; and/or preventing recurrence of infection or biofilm formation.

Therefore, in some embodiments, the nitric oxide released from a particular medicament may provide a particular therapeutic action, such as act as a signaling molecule in a wound healing cascade, act as an anti-inflammatory agent and/or act as an antimicrobial agent. As such, the particular diazeniumdiolate-functionalized polysiloxane macromolecules and the composition of the gel may be tailored to provide the appropriate NO-release profile. Diazeniumdiolates may be triggered to release nitric oxide by exposure to water or another proton source, and an $O^2$-protected diazeniumdiolate may be triggered to release nitric oxide by exposure to light, enzymatic action and/or pH adjustment.

Properties that may be tuned via the pharmaceutically acceptable carrier chosen include hydrophilicity and water uptake. The equilibrium moisture retention for a polymer can vary from 5 percent for certain aliphatic polymers to over 2000 percent for hydrogels and superabsorbent polymers. Thus, in some embodiments, the medicament may include a polymer that has a low equilibrium moisture retention in a range of less than 1 percent to 20 percent. In some embodiments, the medicament may include a polymer that has a moderate equilibrium moisture retention in a range of 20 percent to 200 percent. Further, in some embodiments, the medicament may include a polymer that has a high equilibrium moisture retention of 200 percent or higher. Other excipients may also absorb water and/or be hydrophilic or hydrophobic. In some embodiments, the gel may also include highly water absorbent excipients (e.g., an SAP, a humectant and/or glycerol) if fast release of NO is desired. If slower release of NO is desired, the gel may be more hydrophobic.

For topical medicaments that are gels or include monomers that may form gels upon polymerization, the properties of the gel may be tailored to affect desired NO-release characteristics. Properties of the gel that may be tailored include:

(i) Moisture Vapor Transfer Rate (MVTR)
 The MVTR may be tunable in the gel to match the requirements of a water reactive NO-releasing macromolecule in a gel yet still maintain adequate MVTR for the desired wound or injury area. Gels that maintain a moist wound bed are termed as occlusive. An optimum MVTR maintains a moist wound environment which activates debriding enzymes and growth factors that promote wound healing. Occlusive gels may also act as a barrier towards exogenous microbes, thereby preventing infection. Occlusivity is defined by a MVTR through the wound cover of below 840 $g/m^2$ per 24 hour period.
 (ii) Biodegradability/Bioabsorbability
 Biodegradability refers to the property of the gel to break down into smaller molecular weight components under physiological conditions. Bioresorbability refers to the property by which the wound dressing can break down into smaller molecular weight segments and the segments are completely taken into the body without any biological reaction.
 (iii) Oxygen Permeability
 Adequate oxygen level facilitates neovascularization, aids in collagen synthesis, and may prevent or minimize microbial infection of the wound. Due to damaged vasculature in wounds, there may be a low oxygen tension in the wound bed, leading to hypoxia and anaerobic metabolism that can delay the healing process. Gels may be oxygen permeable so that the wound receives adequate topical oxygen for healing.
 (iv) Nitric Oxide Permeability
 The gel may have adequate permeability towards nitric oxide such that the nitric oxide generated by the NO-releasing macromolecules is available to the wound bed at a desired therapeutic rate. Hydrophilic materials typically have a lower NO permeability towards nitric oxide as compared to hydrophobic materials. The NO permeability of the gel may be matched to the release kinetics of the NO-releasing macromolecule and the rate of water uptake by the polymer, in order to provide for optimal release of NO from the gel.

(v) Ability to Swell

The ability of the gel to swell without dissolution upon contact with wound moisture is beneficial in highly exudating wounds. The gel may serve to imbibe excess moisture that may otherwise cause wound maceration and foul odor.

(vi) Biocompatibility

The gel may be biocompatible, non-toxic, and non-irritable.

(vii) Ionic Character

The ionic character of the gel may affect the surface energy and biocompatibility of the gel. The ionic character of the gel can be quantified by measurement of the zeta potential of the wound dressing material under physiological conditions. Surfaces with highly negative or highly positive zeta potential may be undesirable as they may have an anti- or pro-coagulant effect on the wound and may increase surface energy.

In some embodiments of the invention, at least one property of the gel and/or at least one property of the diazeniumdiolate-functionalized polysiloxane macromolecules may affect the moisture uptake/retention, the moisture vapor transfer rate (MVTR), oxygen permeability, NO permeability, biodegradability/bioabsorbability, biocompatibility and ionic character. The total quantity of nitric oxide stored in the macromolecules, the hydrophobicity/hydrophilicity of the macromolecules and the gel, and the biodegradability/bioresorbability of the macromolecules and the gel control the intrinsic pH, the equilibrium moisture uptake, and regulate diffusion of oxygen into the gel to modulate nitrosative intermediates or the appearance of nitrite/nitrate byproducts. The formation of a polymer gel may also entrap diazeniumdiolate-functionalized polysiloxane macromolecules and prevent or minimize their penetration into the wound bed.

In some embodiments of the invention, the gel is a hydrophobic and non-aqueous gel. The use of an anhydrous and hydrophobic gel may minimize or prevent the release of NO during storage of the formulation. The hydrophic, non-aqueous compositions may also allow for slower diffusion of water required to initiate diazeniumdiolate decomposition and subsequent release of NO to a wound. As such, the gel may be useful for the treatment of acute and/or chronic wounds.

In some embodiments of the invention, the hydrophobic, non-aqueous gel base may be a silicone gel. In particular embodiments, the silicone gel includes cyclomethicone at a concentration in a range of 5 to 30 weight percent and crosslinked polydimethylsiloxane at a concentration in a range of 65 to 85 weight percent. In other embodiments, the hydrophobic, non-aqueous gel base includes polyol at a concentration in a range of 67 to 76 weight percent; electrolyte at a concentration in a range of 0.1 to 2.5 weight percent; silicone polyol at a concentration in a range of 20 to 30 weight percent; and volatile silicone-based solvent at a concentration in a range of 2.5 to 13 weight percent. In other embodiments, the hydrophobic, non-aqueous gel base includes petrolatum at a concentration in a range of 60 to 70 weight percent; dimethiconol at a concentration in a range of 5 to 10 weight percent; and volatile silicone-based solvent.

Further, in other embodiments, the hydrophobic, non-aqueous gel base includes a silicone elastomer at a concentration in a range of 60 to 70 weight percent; and volatile organic solvent at a concentration in a range of 5 to 10 weight percent, and in other embodiments, the hydrophobic, non-aqueous gel base includes silicone elastomer at a concentration in a range of 70 to 80 weight percent; and volatile organic solvent at a concentration in a range of 15 to 20 weight percent.

In addition, in some embodiments, the resulting hydrophobic, non-aqueous gel containing diazeniumdiolate-functionalized polysiloxane macromolecules may have a MVTR below 840 g/m$^2$ per 24 hour period.

Any suitable polyol may be used in the compositions described herein. However, examples of polyols include 1,2-ethanediol, 1,3-propanediol, 1,4-butanediol, 1,6-hexanediol, 1,5-pentanediol, 1,10-decanediol, 2-methyl-1,3-propanediol, 2-methyl-2-butyl-1,3-propanediol, 2,2-dimethyl-1,3-propanediol, 2,2-dimethyl-1,4-butanediol, 2-ethyl-2-butyl-1,3-propanediol, neopentyl glycol hydroxypivalate, diethylene glycol and triethylene glycol.

Any suitable electrolyte may be used. However, examples of electrolytes include sodium chloride, potassium chloride, calcium chloride, and magnesium chloride.

Any suitable silicone polyol may be used. However examples of silicone polyols include dimethicone copolyol, laurylmethicone copolyol, cetyldimethicone copolyol, SilSense® SW-12 dimethicone copolyol ester, SilSense® Copolyol-1 Silicone, Lambent waxes, PEG/PPG-4/12 dimethicone, Bis-PEG/PPG-20/20 dimethicone, PEG/PPG-20/6 dimethicone, PEG/PPG-14/4 dimethicone, and PEG/PPG-20/20 dimethicone.

Any suitable silicone-based solvent may be used. However, examples of silicone-based solvents include cyclomethicone and dimethicone.

Any suitable silicone elastomer may be used. However, examples of silicone elastomers include dimethicone crosspolymer, dimethicone/vinyl dimethicone crosspolymer, cyclopentasiloxane/dimethicone crosspolymer, cetearyl/dimethicone crosspolymer, Wacker Belsil RG-100, ST-Elastomer 10, and trimethylsiloxysilicate/timethiconol crosspolymer.

In some embodiments, the gel includes diazeniumdiolate-functionalized polysiloxane macromolecules, caprylic or capric triglyceride at a concentration in a range of 25 to 55 weight percent; fumed silica at a concentration in a range of 4 to 8 weight percent; cyclomethicone at a concentration in a range of 5 to 20 weight percent; optionally, isopropyl myristate at a concentration in a range of 10 to 85 weight percent; and optionally, mineral oil at a concentration in a range of 10 to 90 weight percent.

In some embodiments, the topical gel includes diazeniumdiolate-functionalized polysiloxane macromolecules and a hydrophilic gel base. In particular embodiments, the concentration of the diazeniumdiolate-functionalized polysiloxane macromolecules is in a range of 0.1 to 2 weight percent. Further, in particular embodiments, the gel includes diazeniumdiolate-functionalized polysiloxane macromolecules, an ethylcellulose polymer at a concentration in a range of 8 to 20 weight percent; and a fatty acid ester at a concentration in a range of 60 to 90 weight percent.

In some embodiments, the gel includes diazeniumdiolate-functionalized polysiloxane macromolecules, polyethylene glycol at a concentration in a range of 15 to 60 weight percent; and propylene glycol at a concentration in a range of 30 to 80 weight percent; crosslinked polyacrylic acid at a concentration in a range of 0.5 to 4.0 weight percent;

optionally, 2-amino-2-methyl propanol at a concentration in a range of 0.05 to 0.15 weight percent; optionally, glycerin at a concentration in a range of 15 to 25 weight percent; and optionally, niacinamide at a concentration in a range of 0.25 to 1.25 weight percent.

In some embodiments, the gel includes diazeniumdiolate-functionalized polysiloxane macromolecules, benzyl alcohol at a concentration in a range of 10 to 30 weight percent; isopropyl alcohol at a concentration in a range of 30 to 75 weight percent; HPC at a concentration in a range of 0.75 to 2.5 weight percent; optionally, 2-amino-2-methyl propanol at a concentration in a range of 0.05 to 0.15 weight percent; optionally, trolamine at a concentration in a range of 0.1 to 1.5 weight percent; optionally, fumed silica at a concentration in a range of 1.0 to 7.0 weight percent; and optionally, niacinamide at a concentration in a range of 0.25 to 1.25 weight percent.

In some embodiments of the invention, the diazeniumdiolate-functionalized polysiloxane macromolecules in the hydrophilic gel may have an octanol/water partition coefficient in a range of −2 to 0. In some embodiments of the invention, the diazeniumdiolate-functionalized polysiloxane macromolecules in the hydrophobic, non-aqueous gel may have an octanol/water partition coefficient in a range of 0.1 to 7.

Methods of Treating Wounds and Skin Ailments

In some embodiments of the invention, provided are methods of treating a wound by applying a topical gel according to an embodiment of the invention. Such methods may be used in combination with any other known methods of wound treatment, including the application of other therapeutic agents, such as those that have anti-inflammatory, pain-relieving, immunosuppressant, vasodilating, wound healing and/or anti-biofilm forming properties. For the methods used herein, additional therapeutic agents and methods may be used prior to, concurrently with or after application with a gel according to embodiments of the invention. Gels according to embodiments of the invention may also be used in any combination with any wound dressings known to those of skill in the art.

In some embodiments of the invention, the topical gels provided herein may be used in conjunction with at least one agent that can disrupt biofilm macrostructure prior to or in conjunction with the application of a wound dressing. In some embodiments, the anti-biofilm agent may disrupt the extracellular matrix of the biofilm. Examples of anti-biofilm agents that may act in this manner include lactoferrin, periodate, xylitol, DNase, protease, an enzyme that degrades extracellular polysaccharides. In some embodiments of the invention, the formulation of the anti-biofilm agent is acidic to promote enzyme activity of the DNase (e.g., mammalian DNases such as DNase II) and the acidic conditions simultaneously may also enhance the rate NO release from diazeniumdiolate macromolecules. In some embodiments, the protease may include at least one of proteinase K, trypsin, Pectinex Ultra SP (PUS) and pancreatin. In some embodiments, enzymes that degrade extracellular polysaccharides may include N-acetylglucosaminidases (e.g., dispersin B).

In some embodiments of the invention, the anti-biofilm agent may act by affecting the transcriptional, translational and/or post-translational regulation of quorum-sensing genes or gene products in the infecting organism(s). For example, the anti-biofilm agents may include at least one of hamamelitannin, cyclic di-GMP and sublethal concentrations of nitric oxide.

The anti-biofilm agents may also act by other mechanisms. For example, the anti-biofilm agent may cause the infecting organism to transition from a sessile state to a metabolically active state. As another example, the anti-biofilm agent may act by causing the infecting organism(s) to transition from a non-motile state to a motile phenotype.

In some embodiments of the invention, the topical gels provided herein may be used in conjunction with a wound debridement procedure. For example, in some embodiments, wounds may first be treated with a debridement procedure; and then a gel according to an embodiment of the invention may be applied to the debrided wound. The medicaments according to embodiments of the invention may increase the rate of wound healing, decrease inflammation and/or exert antimicrobial effect. The wound dressings according to embodiments of the invention may be used in conjunction with any suitable debridement procedure. For example, the debridement procedure may be selective or nonselective.

In some embodiments, the debridement procedure may include at least one of surgical, enzymatic, autolytic, sharp, mechanical and biological processes. Any suitable surgical method may be used, but in some embodiments, the surgical method involves a surgeon cutting away nonviable tissue in the wound. Any suitable enzymatic method may be used, but in some embodiments, the enzymatic method may involve the use of one or more proteases, their required cofactors, and optionally any enhancing agents, to digest the nonviable tissue in the wound. Exemplary proteases include trypsin, papain or other vegetable-derived proteases and collagenase. Any suitable autolytic method may be used, but in some embodiments, the autolytic method involves maintaining a moist wound environment in order to promote the breakdown of nonviable tissue by enzymes that are naturally produced by the body. Any suitable mechanical method may be used, but in some embodiments, the mechanical methods include wet-to-dry gauze, irrigation, pulsatile lavage, whirlpool therapy and/or low frequency ultrasound. Any suitable sharp method may be used, but in some embodiments, the sharp method involves cutting away nonviable tissue by qualified clinical staff (e.g. RN or nurse practitioner). Any suitable biological method may be used, but in some embodiments, the biological method involves the use of maggots which selectively digest the nonviable tissue in the wound. These debridement methods may be used alone or in combination.

After the wound is debrided, a topical gel according to an embodiment of the invention may be applied. Additional processes may be performed and therapeutic agents may be applied. For example, after wound debridement, an anti-biofilm agent may be applied to the wound prior to or in conjunction with the application of the topical gels provided herein. Exemplary anti-biofilm agents include acetylsalicylic acid (aspirin), cyclic di-GMP, lactoferrin, gallium, selenium, as described above. Other compounds, such as hamamelitannin (witch hazel extract), arginine and c-di-GMP, may also be applied.

The gels may be applied to a subject in any suitable manner, such as, for example, rubbing, spreading or placing the gel on the wound or a wound dressing to be in contact with the wound. In some embodiments, the topical gel may be administered to a wound via spray delivery. A non-aqueous delivery propellant may be used for water the sensitive diazeniumdiolate-functionalized polysiloxane macromolecules. Further, in some embodiments, particular components of the gels may be separated at some point prior to application of the medicament. For example, the diazeniumdiolate polysiloxane macromolecule may be stored separately from an aqueous component or propellant until application (e.g., via spraying or applying a gel). In some embodiments, the diazeniumdiolate polysiloxane macromolecule may be combined with an aqueous constituent prior to application of the diazeniumdiolate polysiloxane macromolecules, and in some embodiments, an aqueous constituent may be applied to the wound bed sequentially.

Gels according to some embodiments of the invention may also be used to treat burns. A major goal in the treatment of burns is resuscitation and increase of fluid levels because of the significant loss of water from the body when the barrier function of the skin is compromised. Topical nitric oxide formulations that enhance the barrier function of the skin can not only restore this critical function for maintaining patient vitality but also prevent the infection of burn wound patients as compromised barrier function also creates an easy route for microbial contamination and colonization.

Hydrophobic gels in particular may be advantageous to use in the treatment of burns. Hydrophobic, non-aqueous gels can create an occlusive environment over the burn wounds and so prevent desiccation and create a moist wound environment. In some embodiments, for the treatment of burns, the diazeniumdiolate-funcationalized polysiloxane macromolecules can be loaded in such a gel at different concentrations during different times during the healing process. For example, to prevent infection, a gel may be applied that has a NO loading in a range of 10 μmol NO/g gel to 1 mmol NO/g gel. During later phases of tissue remodeling, for example several weeks after injury, nitric oxide may be loaded at concentrations in a range of 1 nmol NO/g gel to 10 μmol NO/g gel to facilitate healing and matrix remodeling. The moist wound environment created by the occlusive hydrophobic gels enables the release of nitric oxide from the diazeniumdiolate-functionalized polysiloxane macromolecules which is otherwise unexpectedly stable at room temperature in a non-aqueous gel matrix. The diffusion of water throughout the gel matrix thus controls the rate of proton initiated diazeniumdiolate decomposition, favoring faster diazeniumdiolate polysiloxane macromolecular compositions, such as those that have aqueous half-lives in the range of 0.5 minutes to 10 minutes. A rapid NO-release profile for hydrophobic gel matrices may enable these levels of antimicrobial NO release. However, for sustained release of nitric oxide from the gel from hours to days, the hydrophobic matrix coupled with a slowly-degrading diazeniumdiolate-functionalized polysiloxane macromolecule may produce a unique NO-release signature that exhibits a flat release profile.

Gels according to embodiments of the invention may be used to treat acne. Lipophilic diazeniumdiolate-functionalized polysiloxane macromolecules may target the pilosebaceous gland and penetrate the sebum rich environment, for example, as a potential treatment for acne vulgaris. As described above, gels according to embodiments of the invention may include other therapeutic agents. In the case of the treatment of acne, the gels may include other anti-acne agents such as retenoids, such as those described herein. Furthermore, agents such as retenoids may be used in conjunction (prior, concurrently or after) with a gel according to an embodiment of the invention.

Gels according to embodiments of the invention may be used to treat other skin ailments, either via anti-microbial action, anti-inflammatory action, or by any other mechanism. For example, topical gels described herein may be used to treat other skin ailments such as impetigo, psoriasis, tinea pedis, onychomycosis and the like.

Subjects suitable to be treated with a gel according to an embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The invention can also be carried out on animal subjects, particularly mammalian subjects such as mice, rats, dogs, cats, livestock and horses for veterinary purposes, and for drug screening and drug development purposes.

EXAMPLES

Example 1

Synthesis of NO-Releasing Macromolecules

FIG. 1 illustrates the covalent storage of nitric oxide on the aminosilane N-methylaminopropyltrimethoxysilane as a diazeniumdiolate NO donor, followed by co-condensation with a backbone alkoxysilane, tetraethoxysilane, to form Nitricil™ composition 70. Such a NO-releasing macromolecule may be incorporated into medicaments according to some embodiments of the invention.

Example 2

Figures 2A, 2B:
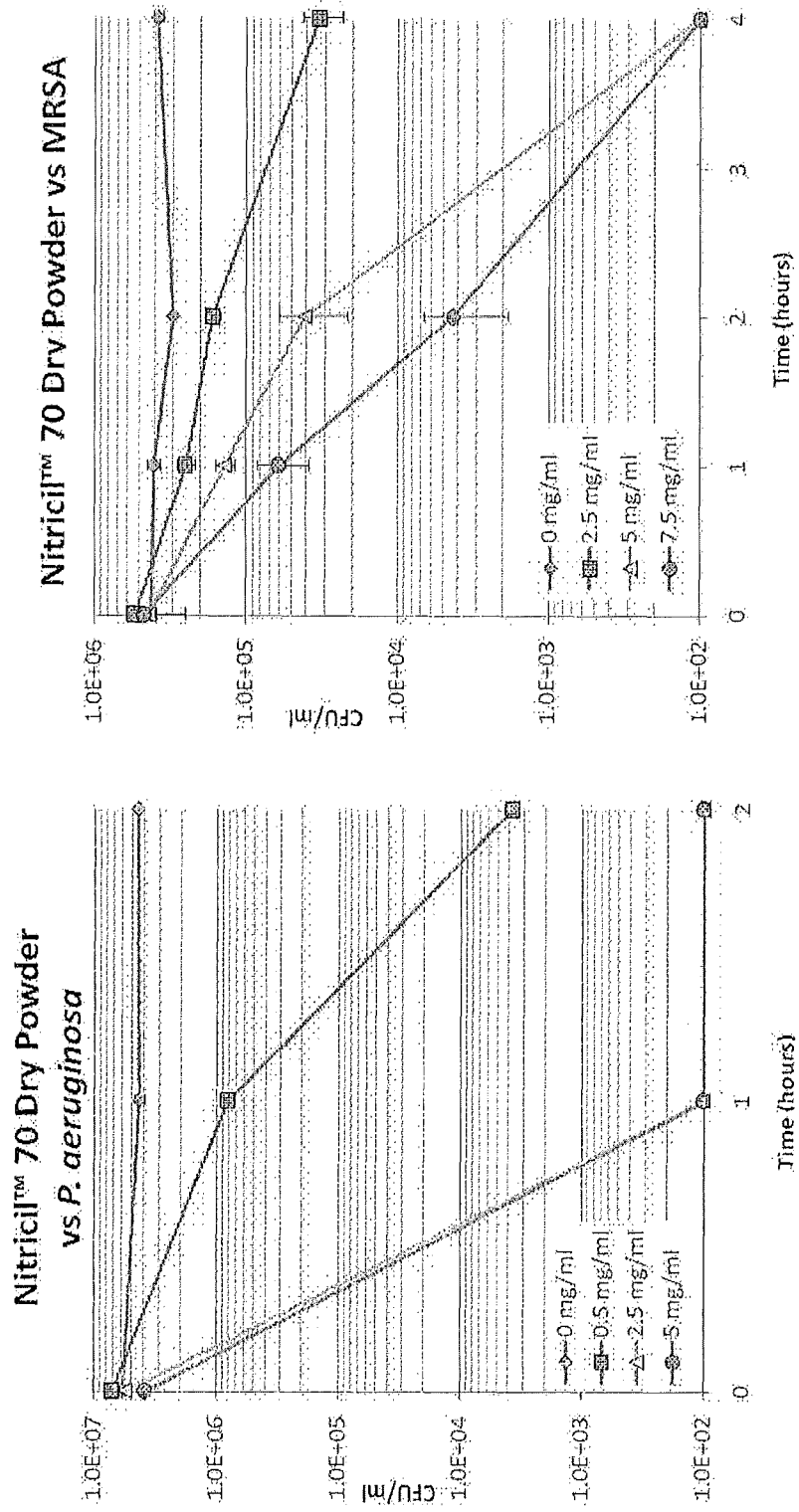
FIG. 2A is a graph illustrating the efficacy of diazeniumdiolate-functionalized polysiloxane macromolecules according to some embodiments of the invention at killing *P. aeruginosa*.
FIG. 2B is a graph illustrating the efficacy of diazeniumdiolate-functionalized polysiloxane macromolecules according to some embodiments of the invention at killing MRSA.

Efficacy of Nitricil™-70 Against Representative Gram-Positive and Gram-Negative Bacteria The antimicrobial efficacy of Nitricil™-70 Dry Powder was assessed against representative multi-drug resistant Gram-positive (HA-MRSA, ATCC 33591, SCCmec Type III) and Gram-negative (*P. aeruginosa*, ATCC 15442) organisms using the ASTM E 2315 Test Method. Various concentrations of NJ070 particles were incubated, in duplicate, with *P. aeruginosa* (See FIG. 2A) or HA-MRSA (See FIG. 2B) at 37° C. in a 1:1000 dilution of Trypticase Soy Broth. At the indicated time points, an aliquot from each culture was serially diluted and plated to quantitate the viable colony forming units (CFU/ml) remaining.

Solid Nitricil™ 70 kills both *P. aeruginosa* and MRSA in a dose- and time-dependent manner, with 99.9 percent killing of *P. aeruginosa* achieved at earlier time points and lower concentrations than are required for HA-MRSA. These data suggest that Nitricil™ is active against both Gram-positive and Gram-negative bacteria, but may be effective against Gram-negative bacteria at lower doses.

Example 3

Efficacy of a Nitricil™ 70 Silicone-Based Gel in Full Thickness Excisional Wounds in a an Infected Rat Animal Model A hydrophobic, non-aqueous NO-releasing gel was formulated using 75 percent Dimethicone/Vinyl Dimethicone Crosspolymer and ~25 percent cyclomethicone co-solvent as a viscosity modifier. Nitricil™-70 at a weight of 24 mg (0.1% w/w final gel loading) or 240 mg (1.0% w/w final gel loading) was dispersed in 6 ml of the cyclomethicone and sonicated to provide a homogenous particle suspension based on the likeness of the silicone solvent and exterior of the co-condensed siloxane particles. The concentrations of the components are listed below in TABLE 1. The Nitricil™ suspension was then combined with dimethicone gel in a 1:3 ratio to provide the finished compositions for animal testing. Blank vehicle contained only dimethicone and cyclomethicone co-solvent absent of any NO-releasing macromolecules.

TABLE 1

| Nitricil ™ 70 | Dimethicone Cross Polymer | Cyclomethicone |
| --- | --- | --- |
| 0.1% | 75% | 24.9% |
| 1.0% | 75% | 24.0% |

Two 2×2 cm full thickness excisional wounds were made on the back of male nude rats across a total of 36 animals broken down into the groups shown in TABLE 2.

TABLE 2

| Group | # of Animals | Test Article | Wound model generation Day 0 | Daily Treatment w/ TA | Innoculation with pseudomonas | Model generation Day 0 | EU & NX Day 1 | EU & NX Day 3 | EU & NX Day 5 | EU & NX Day 7 | EU & NX Day 9 | Total |
| --- | --- | --- | --- | --- | --- | --- | --- | --- | --- | --- | --- | --- |
| A | 8 | Control | Two 2 × 2 cm on rat back | Daily | Day (0) | 8 | 0 | 2 | 2 | 2 | 2 | 8 |
| B | 8 | Blank Vehicle | | Daily | Day (0) | 8 | 0 | 2 | 2 | 2 | 2 | 8 |
| C | 8 | 0.1% Nitricil gel | | Daily | Day (0) | 8 | 0 | 2 | 2 | 2 | 2 | 8 |
| D | 8 | 1.0% Nitricil gel | | Daily | Day (0) | 8 | 0 | 2 | 2 | 2 | 2 | 8 |
| E | 4 | No Treatment | | Daily | Day (0) | 4 | 4 | 0 | 0 | 0 | 0 | 4 |
| TOTAL | 36 | | | | | 36 | 4 | 8 | 8 | 8 | 8 | 36 |
| Balance after each Euthanasia | | | | | | | 32 | 24 | 16 | 8 | 0 | |

Figure 3:
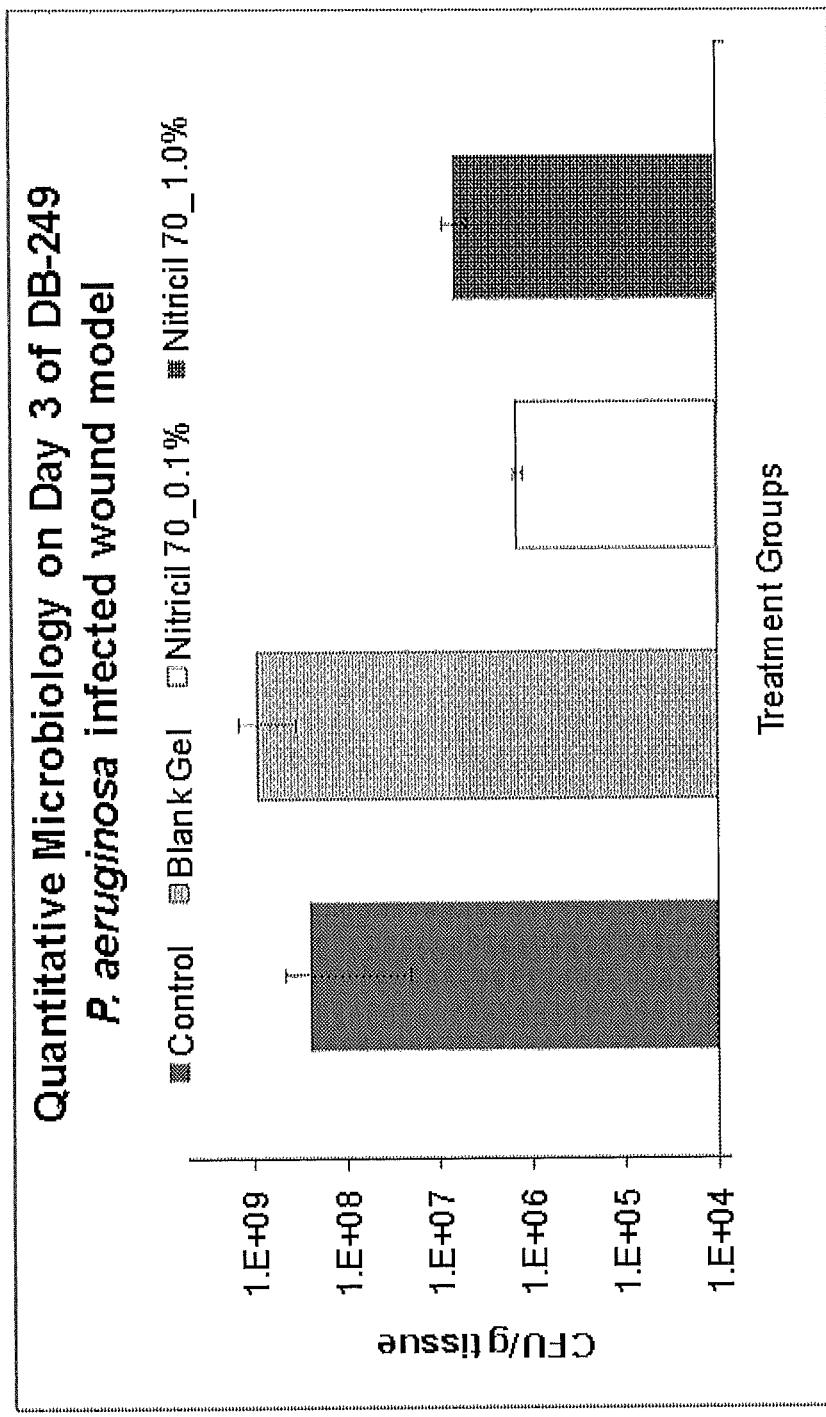
FIG. 3 is a graph illustrating the dose dependence of the efficacy of diazeniumdiolate-functionalized polysiloxane macromolecules according to some embodiments of the invention at killing *P. aeruginosa*.

Immediately following wounding, wounds were challenged with 100 μL of a $10^7$ innoculum of *P. aeruginosa* and covered with Bioclusive Transparent Dressings (Johnson and Johnson) for 24 h to grow mature *P. aeruginosa* biofilms. Treatment with 200 mg of Blank Gel, 0.1 weight percent, and 1.0 weight percent Nitricil™ loaded silicone gels commenced on Day 1 and was repeated once daily for the duration of the study. The occlusive thin film dressings were also replaced following each treatment. On Day 3, two animals from each group were euthanized and 8 mm punch biopsies were taken from the center of each wound, homogenized in sterile saline, and plated to determine the number of colonies per gram of tissue. Referring to FIG. 3, untreated control wounds and blank vehicle treated wounds exhibited $2.5 \times 10^8$ and $9.0 \times 10^8$ CFU/g tissue respectively. However, 0.1 percent Nitricil™ 70 loaded gel demonstrated a >99 percent reduction in the number of *P. aeruginosa* per g tissue with an average value of $1.37 \times 10^6$ CFU/g tissue across the 4 samples taken. The 1.0 percent gel also showed a substantial reduction in comparison to controls at $6.84 \times 10^6$ CFU/g tissue.

Figure 4:
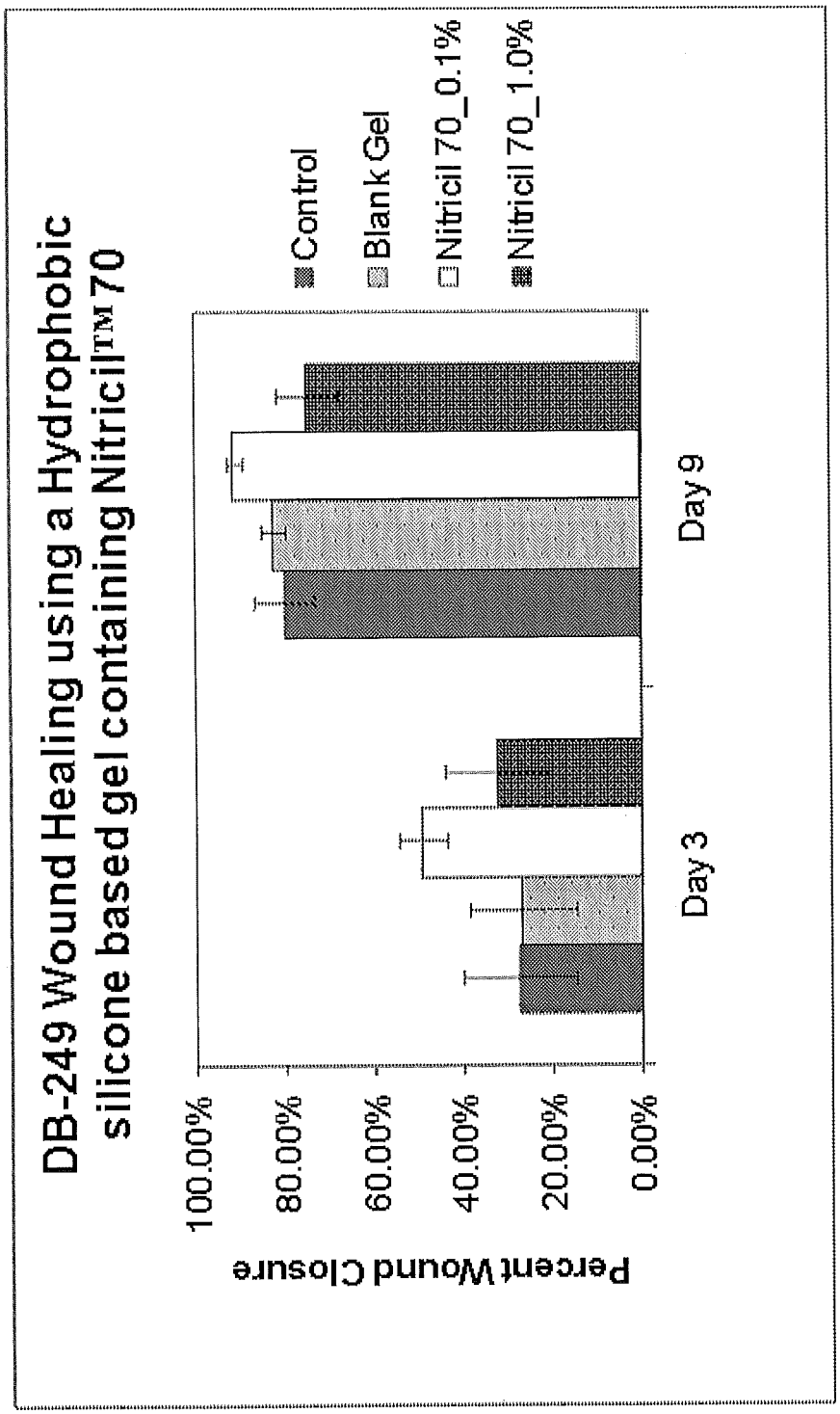
FIG. 4 is a graph illustrating the dose dependence of diazeniumdiolate-functionalized polysiloxane macromolecules according to some embodiments of the invention on wound healing.

Wound photographs were taken at each topical gel application and prior to necropsy. Quantitative measurements of the wound area for each treatment group were performed using the scale bar provided in each photograph. The wound area ($cm^2$) were measured for all wounds available and converted to percent Wound closure when compared to the initial wound area measured for each individual wound. The data for Day 3 and Day 9 are shown in FIG. 4.

Figure 5:
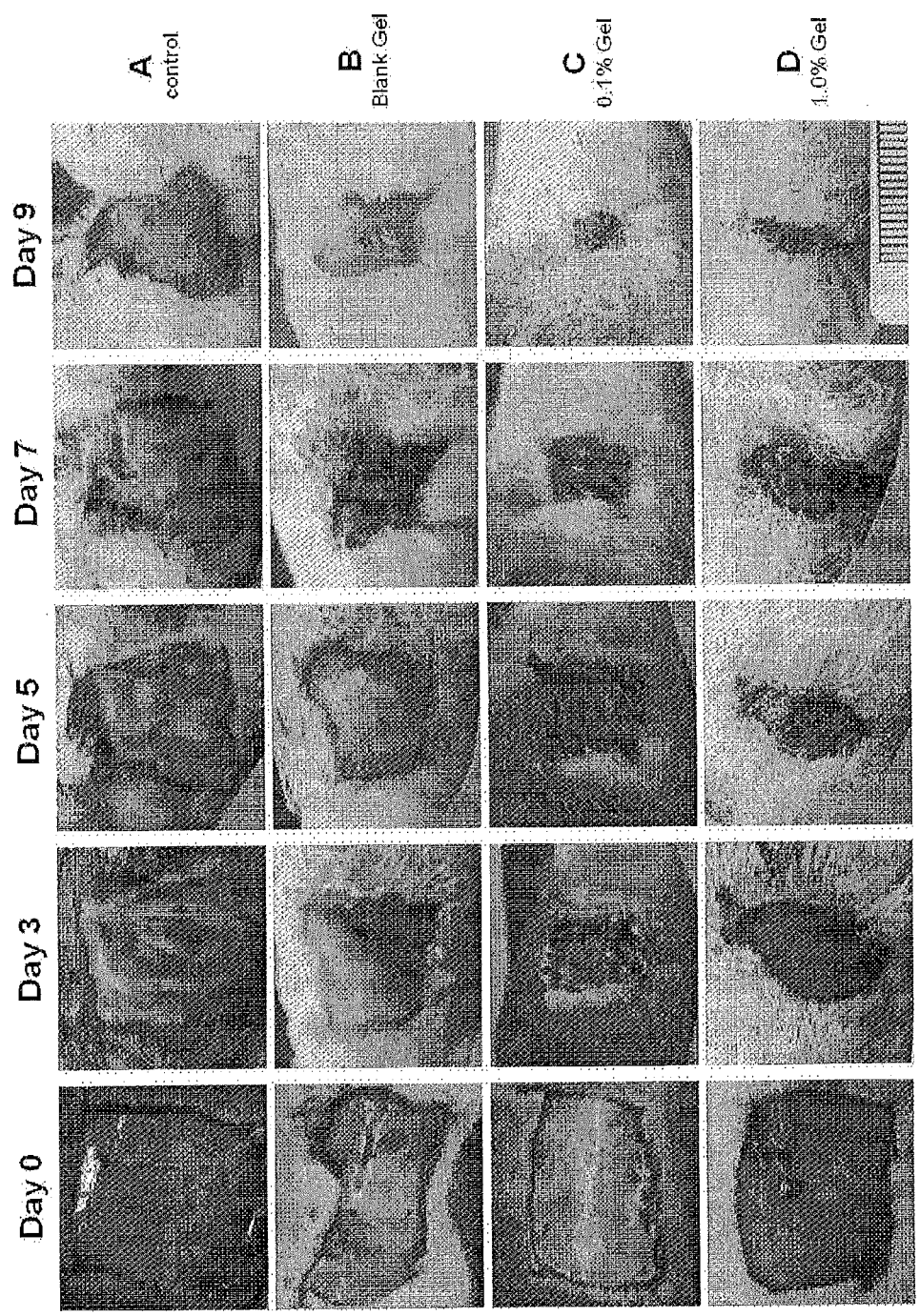
FIG. 5 shows a series of images of wound healing versus time for the graph in FIG. 4.

On Day 3, the 0.1 percent Nitricil™ loaded silicone, gel showed a dramatic enhancement, nearly 25 percent greater wound closure in comparison to all of the other treatment groups. A series of images for all of the treatment groups from Day 0 (wounding) until the completion of the study at Day 9 are shown in FIG. 5.

Example 4

Other Hydrophobic Formulations (Prophetic)

A: Silicone-Based Non-Aqueous Emulsion
  Aqueous formulations containing Nitricil™ in form of a cream that can be applied to the wound bed.
  Prepared by blending Phase A, that includes a polyol such as propylene glycol (67 weight percent to 76 weight %), an electrolyte such as NaCl (0.5 weight %) and the active agent Nitricil™ (1 weight % to 10 weight %) with Phase B, which includes a silicone-based polyol such as dimethicone copolyol (20 to 30 weight %) and a volatile silicone-based solvent such as cyclomethicone (2.5 weight % to 10 weight %).
  Electrolytes such as NaCl may be added to the formulations to stabilize the emulsion.
  Phase A and Phase B are heated separately at 80° C. under nitrogen to preserve diazeniumdiolate NO donor stability and blended together at 800 RPM using a paddle stirrer. Cooled and stored at room temperature.
  The formulation concentrations, shown in % (w/w), are provided in TABLE 3.

TABLE 3

| Phase A | | | Phase B | |
| --- | --- | --- | --- | --- |
| Propylene Glycol | NaCl | Nitricil ™ | Dimethicone coplyol | Cyclomethicone |
| 76% | 0.5% | 1% | 20% | 2.5% |

B: Silicone-Based Ointment
  Non-aqueous ointment based on traditional Petrolatum.
  Includes a Petrolatum bulk (60% to 70%) in addition to dimethiconol (Dimethicone Blend 20, 5% to 10%), in which Nitricil™ has been blended (1% to 10%); a volatile silicone solvent, such as cyclomethicone, is used for viscosity adjustment (10% to 20%).

Dimethicone Blend 20 provides ease of spreading and also may provide a smooth skin-feel.

Under continuous agitation, disperse Nitricil™ in cyclomethicone at room temperature; add Dimethicone Blend 20 at room temperature, followed by addition of Petrolatum heated separately to 75° C.

The formulation concentrations, shown in % (w/w), are provided in TABLE 4.

TABLE 4

| | | Phase B | |
|---|---|---|---|
| Petrolatum | Dimethicone Blend 20 | Cyclomethicone | Nitricil™ |
| 65% | 5% | 20% | 10% |

C: ST-Elastomer Based Non-Aqueous Gel

Non-aqueous gel including a silicone elastomer (70% to 80%) blended with a volatile organic solvent (15% to 20%) containing Nitricil™ (1% to 10%).

May contain isopropyl myristate as emollient (0.5% to 1%).

Dissolve isopropyl myristate in cylomethicone, disperse Nitricil™, add ST-Elastomer 10 under continuous blending.

The formulation concentrations, shown in % (w/w), are provided in TABLE 5.

TABLE 5

| Nitricil™ | ST-Cyclomethicone 5 | ST-Elastomer 10 | Isopropyl Myristate |
|---|---|---|---|
| 5% | 19% | 75% | 1% |

D: Wacker Belsil-Based Non-Aqueous Gel

Non-aqueous gel containing Nitricil™ (1% to 10%), silicone elastomer, Wacker Belsil RG-100 (60% to 80%), blended with a volatile silicone organic solvent (15% to 25%) for viscosity control.

Contains glycerol as emollient (1% to 2%).

Dissolve glycerol in cylomethicone, disperse Nitricil™, add ST-Elastomer 10 under continuous blending.

The formulation concentrations, shown in % (w/w), are provided in TABLE 6.

TABLE 6

| Nitricil™ | ST-Cyclomethicone 5 | Wacker Belsil RG-100 | Glycerol |
|---|---|---|---|
| 2% | 18% | 78% | 2% |

Example 5

Antimicrobial Activity of a Nitricil™ 70 Based Hydrophilic Gel Against MRSA Biofilms A hydrophilic, NO-releasing gel was formulated using glycerol as the base. Carbopol 940 was used as rheology modifier. Briefly, Carbopol 940 was dissolved in glycerol at a concentration of 0.5% (w/v) by overnight stirring of 0.1 g Carbopol 940 in 20 ml glycerol at 50° C. In a separate container, 200 μl of triethanolamine was added to 10 ml glycerol, to adjust the pH to 11.0.

Nitricil™-70 at a weight of 18.93 mg (1% w/w final gel loading) or 189.3 mg (10% w/w final gel loading) was dispersed in 1 ml of the glycerol at pH 11.0, using a paddle stirrer at 500 RPM. A half milliliter of the 0.5% Carbopol 940 solution was added to the Nitricil™-70 dispersion under continuous, agitation at 500 RPM. The resulting viscous gel was transferred to a 3 ml polypropylene syringe. The pH of the gel was measured to be 7.0.

The formulation concentrations, shown in % (w/w), are provided in TABLE 7

TABLE 7

| Nitricil | Carbopol 940/941 | Glycerol |
|---|---|---|
| 1% | 0.13% | 98.87% |
| 10% | 0.13% | 89.87% |

Figure 6:
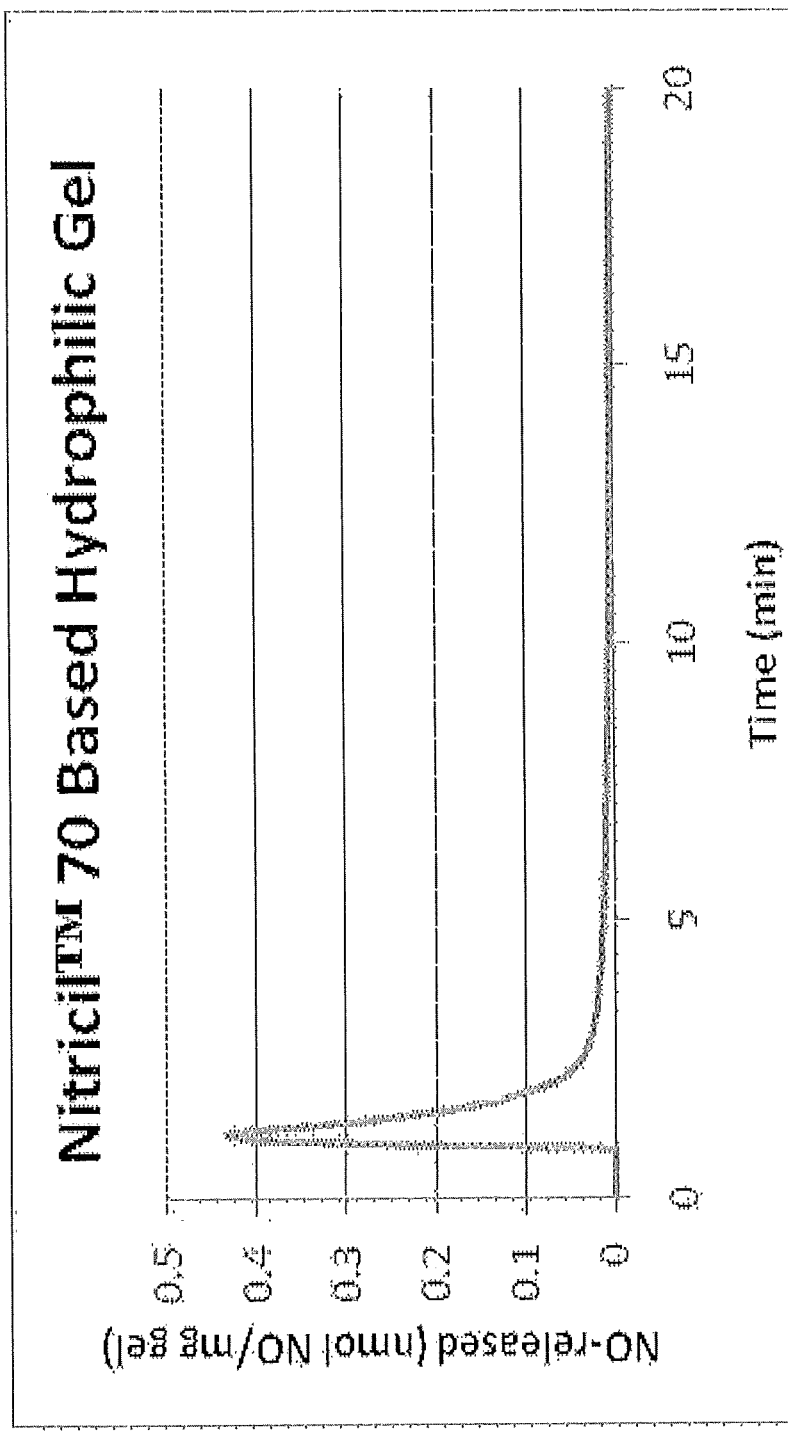
FIG. 6 provides the NO-release versus time for a gel according to an embodiment of the invention.

The NO-release of the gel was measured by weighing a small amount of the gel (2.8 mg) into the Chemiluminescent Nitric Oxide Analyzer, as shown in FIG. 6.

MRSA colony biofilms were grown on UV-sterilized 25 mm polycarbonate filters (0.22 μm) as described previously (Anderl et al 2000, Rani et al 2007). Briefly, an overnight culture of *S. aureus* ATCC 33591 was diluted to $OD_{600}$ of approximately 0.1. Ten microliters of the diluted culture was spotted in the center of a polycarbonate filter resting on a tryptic soy agar plate. Biofilms were grown for two days at 37° C., with a transfer to a new TSA plate after 24 h. At the initiation of the experiment, each filter was transferred to an individual well in a 6-well plate. Gel formulations (0.1 ml) were added drop-wise over top of each biofilm (three biofilms per treatment) without disrupting the biofilm structure. Plates were incubated inside at humidified box (37° C., 24 h). After 24 h, Letheen broth (1 ml) was used to wash each well and then added, along with each filter, to 9 ml of Letheen broth in a 50 ml conical. Conicals were sonicated (1 min) and vortexed (1 min). The resulting bacterial suspension was serially diluted and plated to obtain colony counts. The results are shown in TABLES 8 and 9.

TABLE 8

Raw Data for Nitricil ™ 70 Hydrophilic Gel versus MRSA biofilms

| Sample Id | Rep | Time | CFU/ml | Log CFU | % Red | Log Red |
|---|---|---|---|---|---|---|
| No treatment | 1 | 24 h | 1.46E+09 | 9.16 | −26.8 | −0.12 |
| No treatment | 2 | | 7.98E+08 | 8.90 | 30.6 | 0.15 |
| No treatment | 3 | | 1.19E+09 | 9.08 | −3.8 | −0.03 |
| HG-CONTROL-003 | 1 | 24 h | 1.63E+08 | 8.21 | 85.8 | 0.84 |
| HG-CONTROL-003 | 2 | | 1.68E+08 | 8.23 | 85.4 | 0.82 |
| HG-CONTROL-003 | 3 | | 1.60E+08 | 8.20 | 86.1 | 0.84 |

TABLE 8-continued

Raw Data for Nitricil ™ 70 Hydrophilic Gel versus MRSA biofilms

| Sample Id | Rep | Time | CFU/ml | Log CFU | % Red | Log Red |
|---|---|---|---|---|---|---|
| 01-00009-002-HG-01-0001 | 1 | 24 h | 1.40E+06 | 6.15 | 99.88 | 2.90 |
| 01-00009-002-HG-01-0001 | 2 | | 1.12E+06 | 6.05 | 99.90 | 3.00 |
| 01-00009-002-HG-01-0001 | 3 | | 3.32E+06 | 6.52 | 99.7 | 2.53 |
| 01-00009-002-HG-10-0001 | 1 | 24 h | 1.00E+03 | 3.00 | 99.99991 | 6.05 |
| 01-00009-002-HG-10-0001 | 2 | | 1.00E+03 | 3.00 | 99.99991 | 6.05 |
| 01-00009-002-HG-10-0001 | 3 | | 3.10E+03 | 3.49 | 99.9997 | 5.56 |

TABLE 9

Data Summary for Nitricil ™ 70 Hydrophilic Gel versus MRSA biofilms

| | | Average | | | |
|---|---|---|---|---|---|
| Test Article | Time | CFU/ml | Log CFU | % Red | Log Red |
| No treatment | 24 h | 1.15E+09 | 9.05 | 0.00 | 0.00 |
| HG-CONTROL-003 | 24 h | 1.64E+08 | 8.21 | 85.8 | 0.83 |
| 01-00009-002-HG-01-0001 | 24 h | 1.95E+06 | 6.24 | 99.8 | 2.81 |
| 01-00009-002-HG-10-0001 | 24 h | 1.70E+03 | 3.16 | 99.9999 | 5.88 |

Example 6

Other Hydrophilic Formulations (Prophetic)

A: Ethocel Based Non-Aqueous Gel

Non-aqueous gel including ethylcellulose polymers dissolved in propylene glycol dicaprylate/dicaprate (Miglyol).

The ethylcellulose polymers are used as pharmaceutical excipients, tablet binders, etc. and Miglyol solvent has inherent emollient properties due to its plant triglyceride base.

The polymers Ethocel Std 7 FP Premium (11-16%), Ethocel Std 10 FP Premium (11-16%), Ethocel Std 100 FP Premium (7 to 12%) will be used. These concentrations are lower for 100 FP due to its longer chain length. Miglyol 840 solvent will be used (80% to 85%). Nitricil concentration will be varied from 1 to 10%.

Formulations with various Ethocel polymers are shown in TABLES 10-12.

TABLE 10

Ethocel Std 7 FP Premium

| Nitricil ™ | Ethocel St 7 FP | Miglyol 840 |
|---|---|---|
| 1% | 16% | 83% |
| 2% | 14% | 84% |
| 5% | 12.5% | 82.5% |
| 10% | 11% | 79% |

TABLE 11

Ethocel Std 10 FP Premium

| Nitricil ™ | Ethocel St 10 FP | Miglyol 840 |
|---|---|---|
| 1% | 16% | 83% |
| 2% | 14% | 84% |
| 5% | 12.5% | 82.5% |
| 10% | 11% | 79% |

TABLE 12

Ethocel Std 100 FP Premium

| Nitricil ™ | Ethocel St 100 FP | Miglyol 840 |
|---|---|---|
| 1% | 12% | 87% |
| 2% | 10% | 88% |
| 5% | 8.5% | 86.5% |
| 10% | 7% | 83% |

Example 7

Nitric Oxide Stability as a Function of Gel Excipients

A series of topical gels were formulated to contain nitric oxide-releasing silica particles in weight percentages ranging from 0.1% to 2.0% wt/wt and the percentage of nitric oxide recovered from the formulated gel prototypes was measured via nitric oxide chemiluminescence. Not all excipient combinations were able to maintain diazeniumdiolate NO-donor stability (TABLE 16). Unexpectedly, a series of topical gels containing diazeniumdiolate modified silica that exhibited stability at room temperature were discovered.

TABLE 13

Gels comprising Cab-O-Sil as the thickening agent (% wt/wt)

| ID | Nitricil ™ | CCTG | Isopropyl myristate | Cab-O-Sil M5P | Cyclomethicone | Mineral Oil | PPG-15 |
|---|---|---|---|---|---|---|---|
| A | 0.1% | 50.4% | 42.0% | 7.5% | | | |
| B | 0.1% | | | 7.5% | 10% | 82.4% | |
| C | 1.0% | 51.0% | 42.0% | 6.0% | | | |
| D | 1.0% | | | 6.0% | 13.0% | 80.0% | |
| E | 1.0% | 49.5% | 42.0% | 7.5% | | | |
| F | 1.0% | | | 7.5% | 10.0% | 82.5% | |
| G | 1.0% | | | 8.0% | 10.0% | 82.0% | |
| H | 1.0% | 29% | | 5.0% | | 49.0% | 16.0% |
| I | 1.0% | 29% | | 7.0% | | 47.0% | 16.0% |
| J | 1.0% | 52% | | 5.0% | 13% | 13.0% | 16.0% |

TABLE 14

Gels comprising Carbopol 980 as the thickening agent (% wt/wt)

| ID | Nitricil ™ | PEG 300 | Propylene glycol | Carbopol 980 | Glycerin | AMP | Niacinamide |
|----|-----------|---------|------------------|--------------|----------|------|-------------|
| K  | 0.1%      | 20.0%   | 62.1%            | 0.65%        | 17.0%    | 0.10% |            |
| L  | 0.1%      |         | 76.0%            | 0.80%        | 23.0%    | 0.10% |            |
| M  | 1.0%      | 57.1%   | 41.0%            | 0.80%        |          | 0.10% |            |
| N  | 1.0%      | 56.8%   | 41.0%            | 1.0%         |          | 0.15% |            |
| O  | 1.0%      | 55.7%   | 41.0%            | 1.0%         |          |       | 1.25%      |

TABLE 15

Alcohol based gels (% wt/wt)

| ID | Nitricil ™ | Benzyl alcohol | IPA   | HPC   | AMP  | Niacinamide | Trolamine | Cab-O-Sil M5P |
|----|-----------|----------------|-------|-------|------|-------------|-----------|---------------|
| P  | 2.0%      | 25.0%          | 71.0% | 2.0%  |      |             |           |               |
| Q  | 2.0%      | 25.0%          | 69.0% | 1.75% |      | 1.25%       | 1.0%      |               |
| R  | 2.0%      | 25.0%          | 68.0% | 1.0%  |      |             | 1.0%      | 3.0%          |
| S  | 2.0%      | 25.0%          | 71.1% | 1.75% | 0.1% |             |           |               |

TABLE 16

% Nitric Oxide remaining in the Gel following initial formulation of excipients as a measure of stability performance (ND = not determined)

| ID | % NO Remaining |
|----|----------------|
| A  | ND             |
| B  | ND             |
| C  | 74%            |
| D  | 100%           |
| E  | 100%           |
| F  | 82%            |
| G  | 94%            |
| H  | 97%            |
| I  | 71%            |
| J  | 93%            |
| K  | ND             |
| L  | 15%            |
| M  | 83%            |
| N  | 54%            |
| O  | 59%            |
| P  | 70%            |
| Q  | 70%            |
| R  | 72%            |
| S  | ND             |

Figure 7:
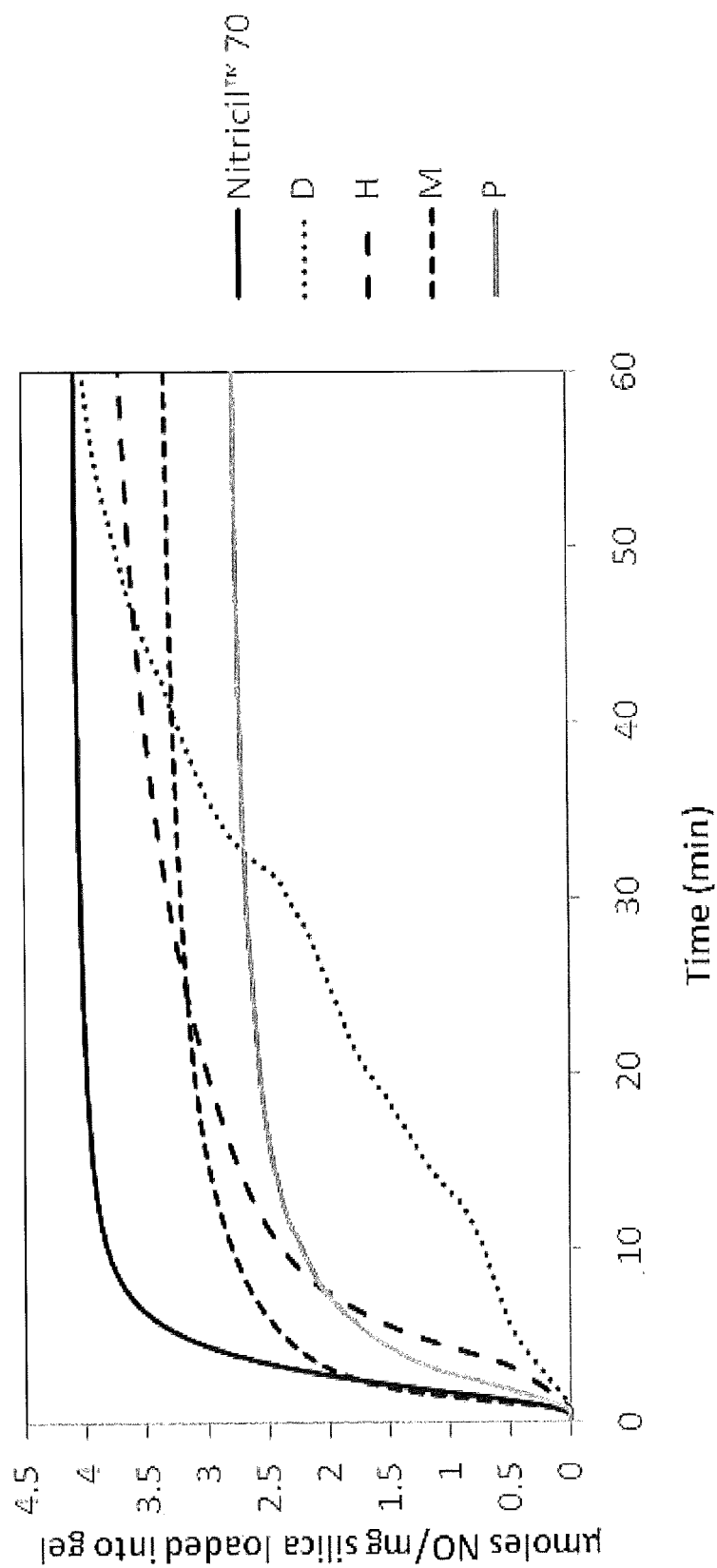
FIG. 7 shows NO-release curves showing change in kinetic profile as a function of excipients versus diazeniumdiolate-functionalized polysiloxane macromolecules alone.
Figure 8:
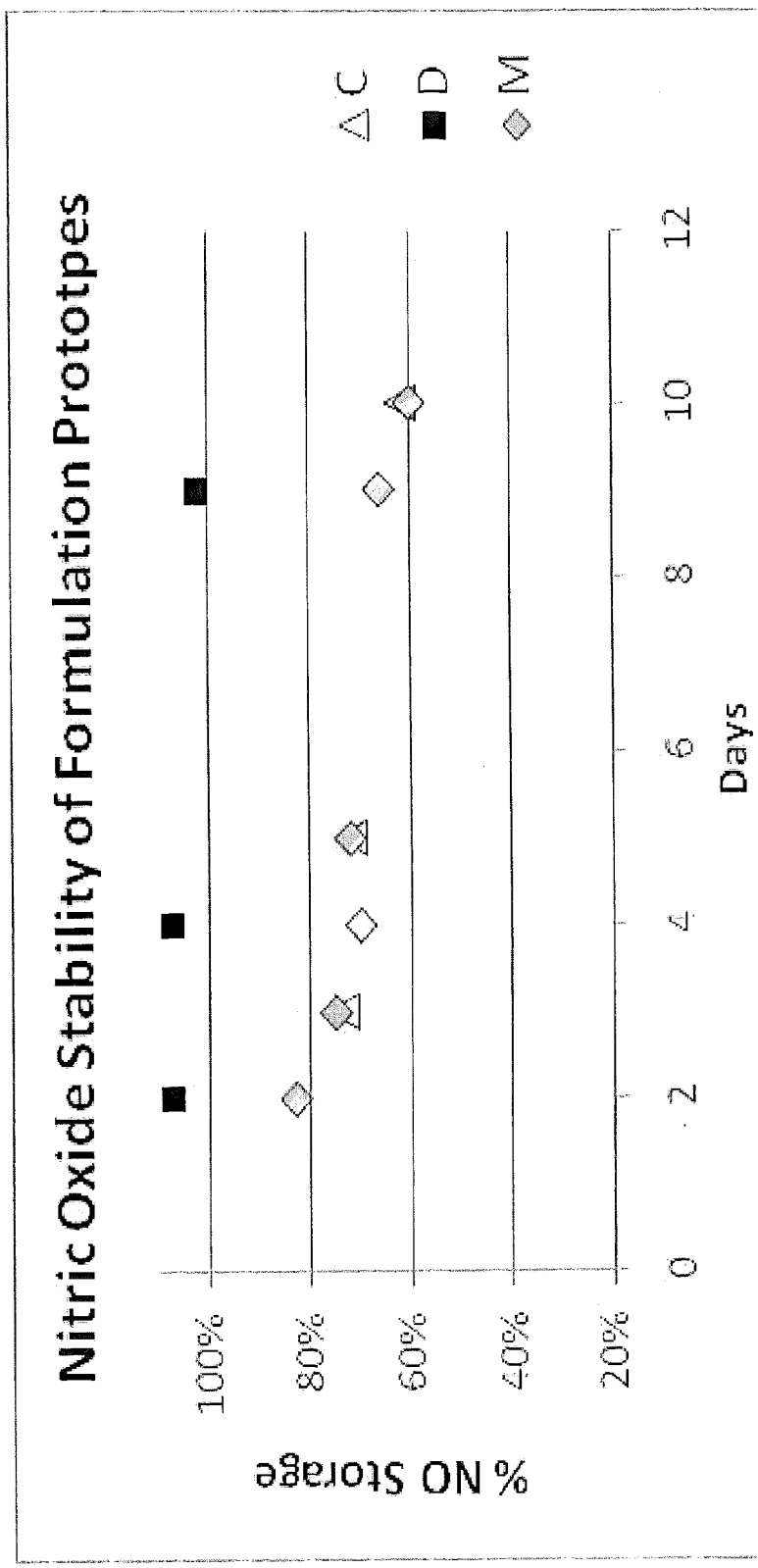
FIG. 8 shows the NO stability in gel over time decreases as a function of gel components.
Figure 9:
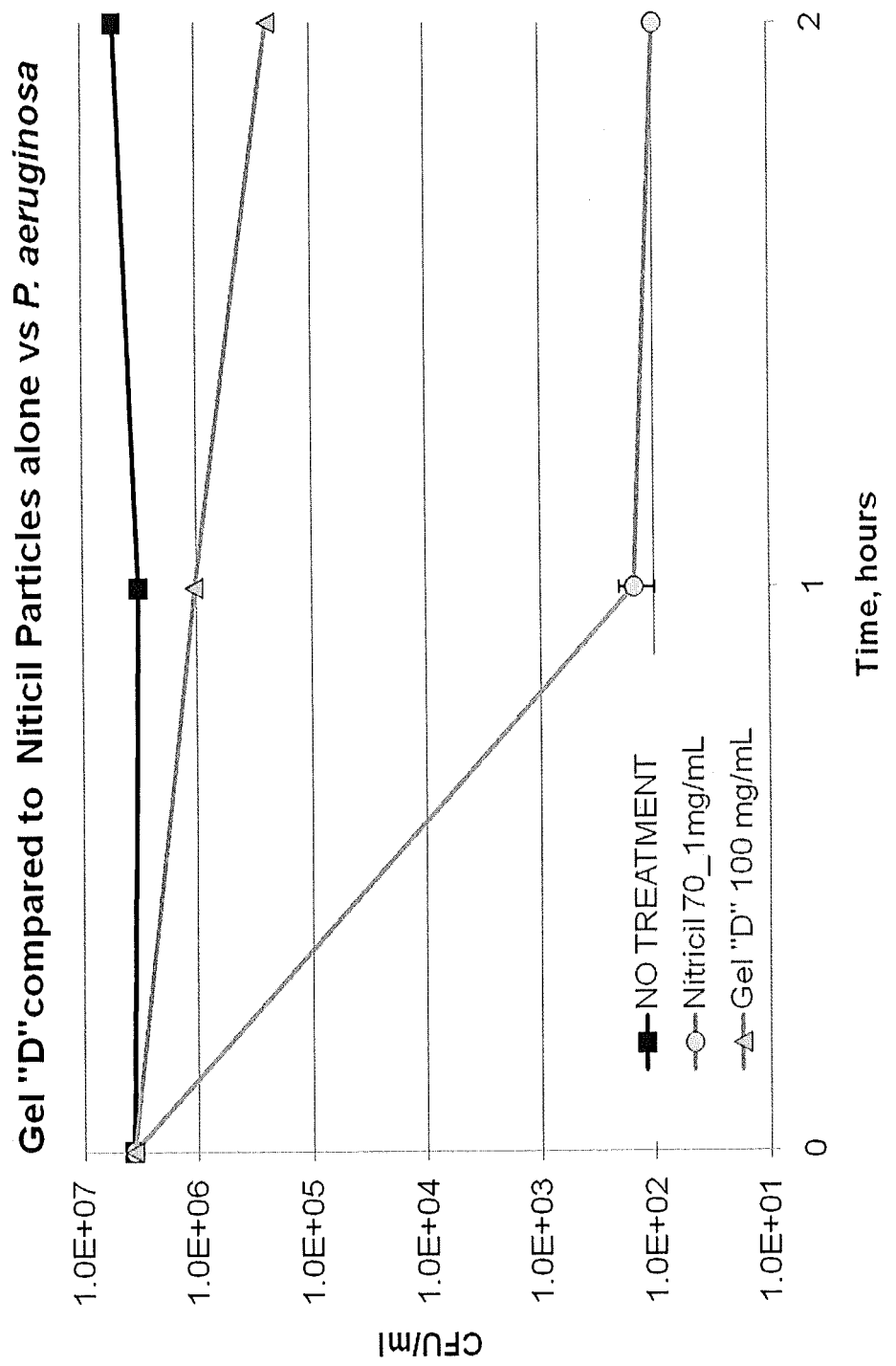
FIG. 9 shows the antimicrobial time-kill of *P. aeruginosa* for diazeniumdiolate-functionalized polysiloxane macromolecules vs. formulated hydrophobic gel at equivalent concentrations of silica.
Figure 10:
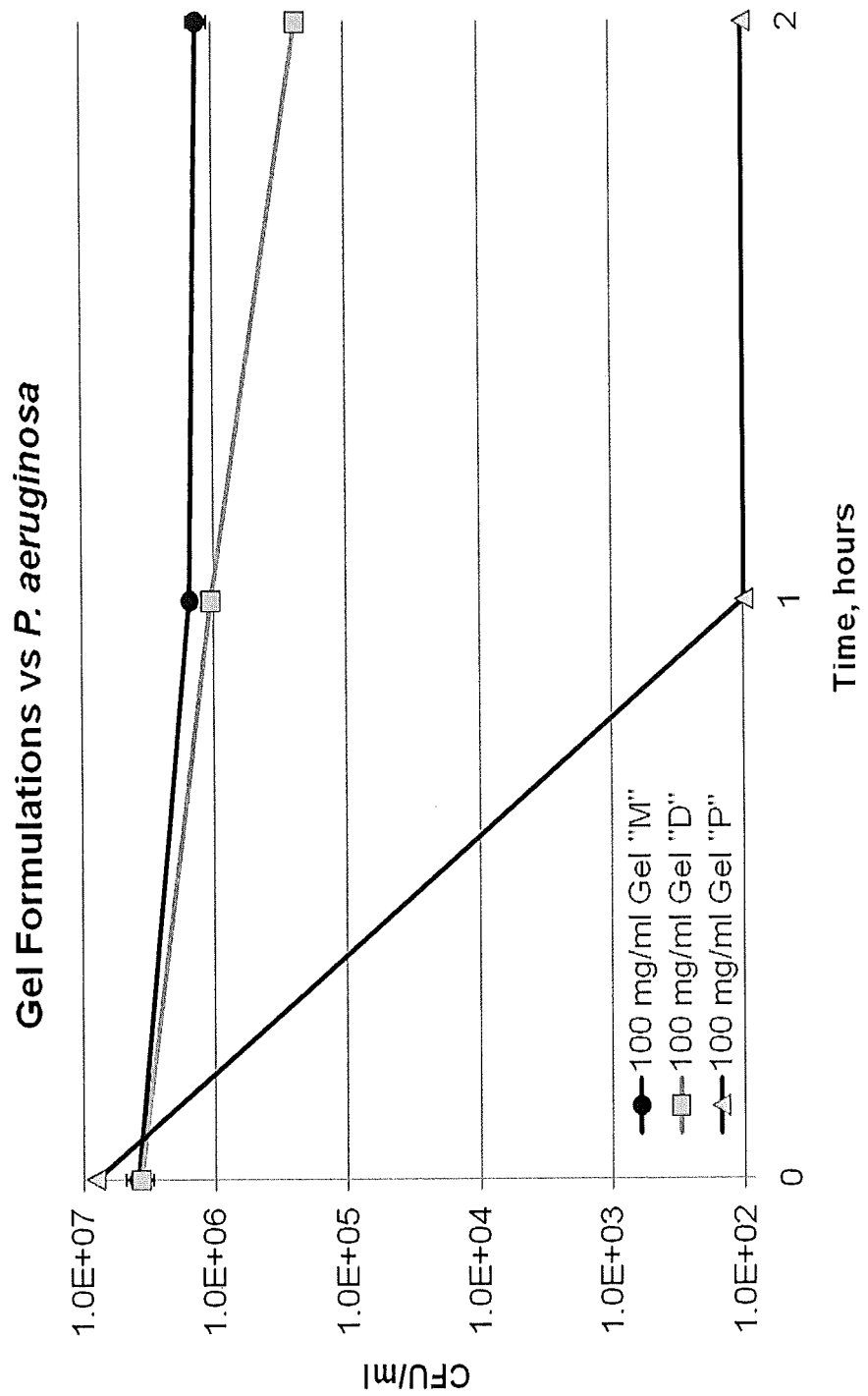
FIG. 10 shows the hydrophilic vs. hydrophobic gel time kill efficacy against *P. aeruginosa* for particular gels according to some embodiments of the invention.
Figure 11:
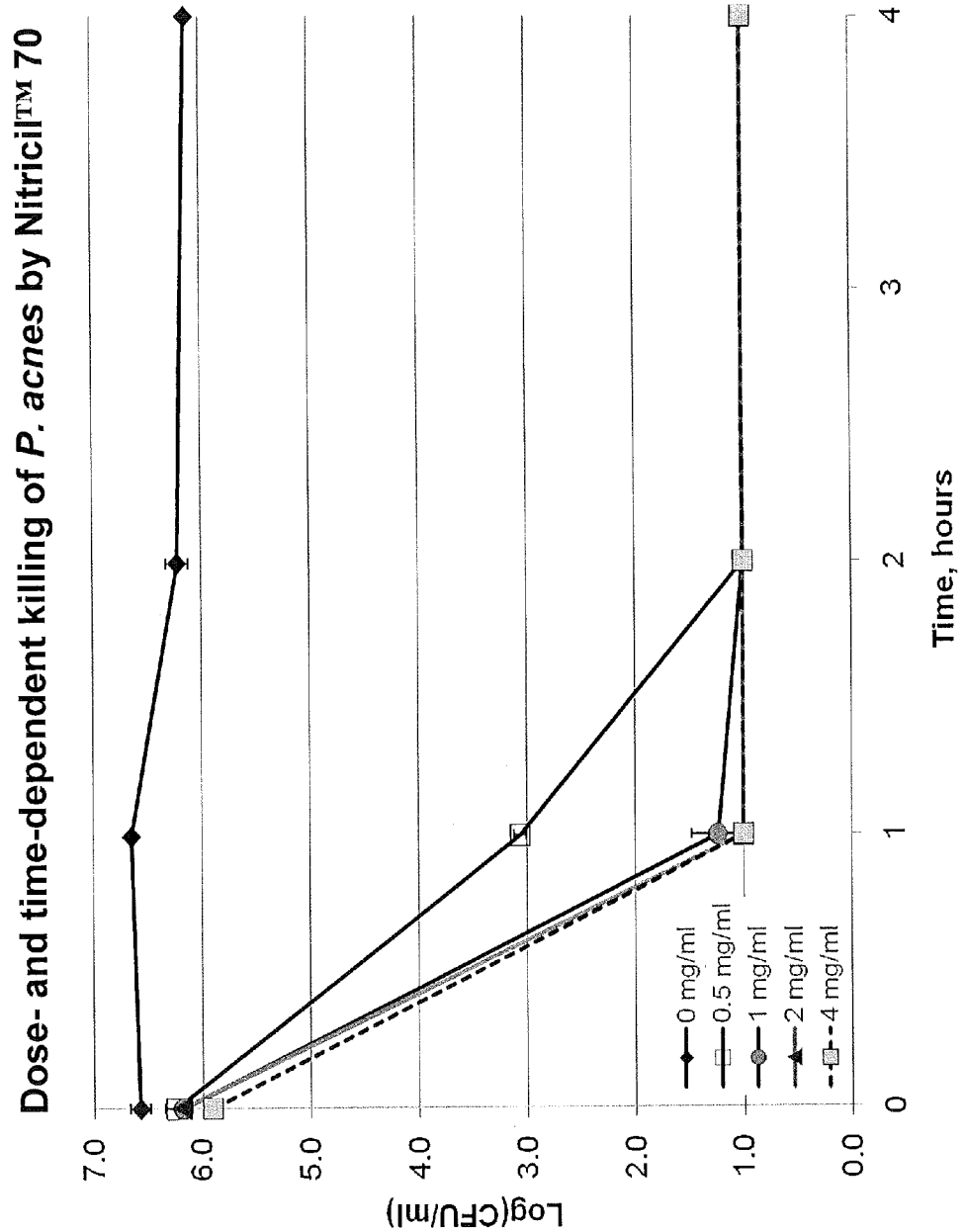
FIG. 11 shows the dose and time kill efficacy of diazeniumdiolate-functionalized polysiloxane macromolecules according to an embodiment of the invention against *P. acnes*.
Figure 12:
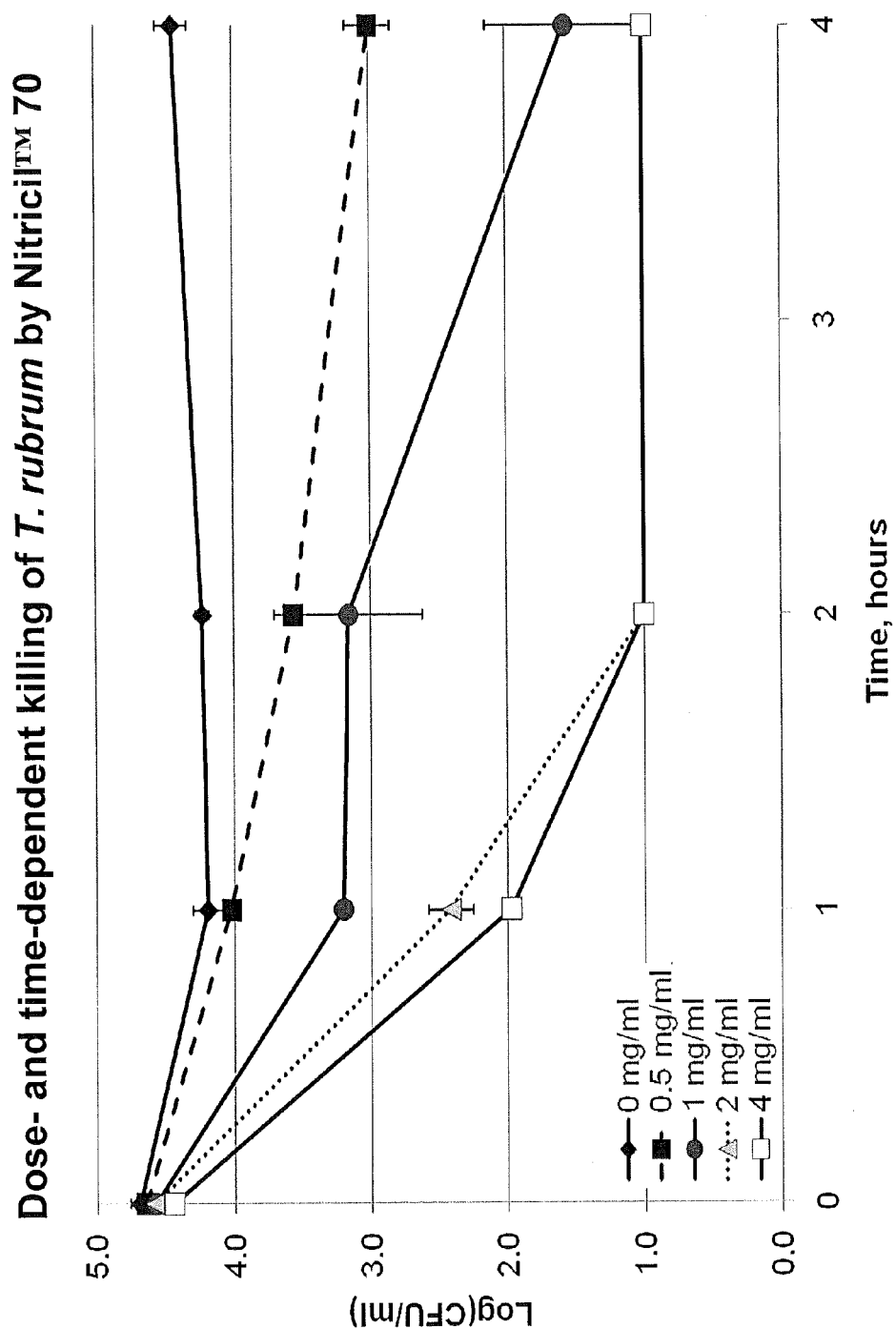
FIG. 12 shows the dose and time kill efficacy of diazeniumdiolate-functionalized polysiloxane macromolecules according to an embodiment of the inveniton against *T. rubrum*.

FIG. 7 shows NO-release curves showing change in kinetic profile as a function of excipients versus Nitricil alone. FIG. 8 shows the NO stability in gel over time decreases as a function of gel components. FIG. 9 shows the antimicrobial Time-kill of gels showing Nitricil vs. formulated hydrophobic gel at equivalent concentrations of silica prolonging release versus *P. aeruginosa*. FIG. 10 shows the hydrophilic vs. hydrophobic gel time kill efficacy against *P. aeruginosa*. FIG. 11 shows the does and time kill efficacy against *P. acnes*. FIG. 12 shows the dose and time kill efficacy against *T. rubrum*.

We claim:

1. A topical composition comprising nitric oxide-releasing polysiloxane macromolecules and a hydrophobic, non-aqueous gel base, the hydrophobic, non-aqueous gel base comprising mineral oil, wherein the nitric oxide (NO) storage per gram is in a range of 100 nmol NO/g to 1 mmol NO/g of the topical composition and at least 70% of NO of the nitric oxide-releasing polysiloxane macromolecule remains in the topical composition two days after initial formulation when the topical composition is stored at room temperature.

2. The topical composition of claim 1, wherein the concentration of the nitric oxide-releasing polysiloxane macromolecules is in a range of 0.1% to 20% by weight of the topical composition.

3. The topical composition of claim 1, wherein the hydrophobic, non-aqueous gel base is a silicone gel.

4. The topical composition of claim 1, wherein the hydrophobic, non-aqueous gel base comprises petrolatum.

5. The topical composition of claim 1, wherein mineral oil is present in the topical composition at a concentration in a range of 10% to 90% by weight of the topical composition.

6. The topical composition of claim 1, wherein the hydrophobic, non-aqueous gel base comprises gel excipients and the nitric oxide-releasing polysiloxane macromolecules and gel excipients have an octanol/water partition coefficient in a range of 0.1 to 7.

7. The topical composition of claim 1, wherein the nitric oxide-releasing polysiloxane macromolecules have a hydrodynamic radius in a range of 1000 nm to 10 microns.

8. The topical composition of claim 1, wherein the nitric oxide-releasing polysiloxane macromolecules have a hydrodynamic radius in a range of 1 nm to 100 nm.

9. The topical composition of claim 1, further comprising an anti-acne agent, antimicrobial agent, benzoyl peroxide, or a corticosteroid.

10. A topical composition comprising nitric oxide-releasing polysiloxane macromolecules and a hydrophilic gel base, the hydrophilic gel base comprising an alcohol, wherein the nitric oxide (NO) storage per gram is in a range of 100 nmol NO/g to 1 mmol NO/g of the topical composition and at least 70% of NO of the nitric oxide-releasing polysiloxane macromolecule remains in the topical composition two days after initial formulation when the topical composition is stored at room temperature.

11. The topical composition of claim 10, wherein the concentration of the nitric oxide-releasing polysiloxane macromolecules is in a range of 0.1% to 20% by weight of the topical composition.

12. The topical composition of claim 10, further comprising isopropyl alcohol at a concentration in a range of 60% to 90% by weight of the topical composition; and hydroxypropyl cellulose at a concentration in a range of 0.75% to 2.5% by weight of the topical composition.

13. The topical composition of claim 10, wherein the hydrophilic gel base comprises gel excipients and the nitric oxide-releasing polysiloxane macromolecules and the gel excipients have an octanol/water partition coefficient in a range of −2 to 0.

14. The topical composition of claim 10, wherein the nitric oxide-releasing polysiloxane macromolecules have a hydrodynamic radius in a range of 1000 nm to 10 microns.

15. The topical composition of claim 10, wherein the nitric oxide-releasing polysiloxane macromolecules have a hydrodynamic radius in a range of 1 nm to 100 nm.

16. The topical composition of claim 10, further comprising a retinoid, antimicrobial agent, benzoyl peroxide, or a corticosteroid.

17. A method of treating a wound comprising applying the topical composition of claim 1.

18. A method of treating a wound comprising applying the topical composition of claim 10.

19. A method of treating a burn comprising applying the topical composition of claim 1.

20. A method of treating acne comprising applying the topical composition of claim 1.

21. A method of treating acne comprising applying the topical composition of claim 10.

22. The topical composition of claim 1, wherein at least 80% of NO of the nitric oxide-releasing polysiloxane macromolecule remains in the topical composition two days after initial formulation when the topical composition is stored at room temperature.

23. The topical composition of claim 10, wherein at least 80% of NO of the nitric oxide-releasing polysiloxane macromolecule remains in the topical composition two days after initial formulation when the topical composition is stored at room temperature.

24. The topical composition of claim 1, wherein the topical composition comprises one or more hydrophobic components and the total concentration of the one or more hydrophobic components present in the topical composition is at least 49% by weight of the topical composition.

25. The topical composition of claim 1, wherein the topical composition comprises one or more hydrophobic components and the total concentration of the one or more hydrophobic components present in the topical composition is at least 80% by weight of the topical composition.

26. The topical composition of claim 10, wherein the alcohol is present in the topical composition at a concentration of at least 60% by weight of the topical composition.

27. The topical composition of claim 10, wherein the alcohol is present in the topical composition at a concentration in a range of 60% to 90% by weight of the topical composition.

28. The topical composition of claim 10, wherein the alcohol is isopropyl alcohol.

29. The topical composition of claim 10, wherein the hydrophilic gel base further comprises hydroxypropyl cellulose.

30. The topical composition of claim 29, wherein the hydroxypropyl cellulose is present at a concentration in a range of 0.75% to 2.5% by weight of the composition.

31. The topical composition of claim 10, wherein the topical composition is non-aqueous.

* * * * *

UNITED STATES PATENT AND TRADEMARK OFFICE
CERTIFICATE OF CORRECTION

Page 1 of 2

PATENT NO. : 9,526,738 B2
APPLICATION NO. : 13/256928
DATED : December 27, 2016
INVENTOR(S) : Stasko et al.

It is certified that error appears in the above-identified patent and that said Letters Patent is hereby corrected as shown below:

On the Title Page

Please delete Title Page and replace with attached Title Page

In the Claims

Column 30, Line 32, Claim 3: Please correct "non-aqueous gel base is a silicone gel."
  to read -- non-aqueous gel base further comprises a silicone gel. --
 Line 34, Claim 4: Please correct "non-aqueous gel base comprises"
  to read -- non-aqueous gel base further comprises --
 Line 39, Claim 6: Please correct "non-aqueous gel base comprises"
  to read -- non-aqueous gel base further comprises --

Column 31, Line 4, Claim 13: Please correct "hydrophilic gel base comprises gel"
  to read -- hydrophilic gel base further comprises gel --

Column 32, Line 33: Please insert the following two claims:
-- 32. The topical composition of claim 10, wherein the alcohol is present in the topical composition at a concentration in a range of 20% to 90% by weight of the topical composition.

33. The topical composition of claim 10, wherein the alcohol is present in the topical composition at a concentration up to 60% by weight of the topical composition. --

Signed and Sealed this
Thirteenth Day of February, 2018

Andrei Iancu
*Director of the United States Patent and Trademark Office*

(12) United States Patent
Stasko et al.

(10) Patent No.: US 9,526,738 B2
(45) Date of Patent: Dec. 27, 2016

(54) TOPICAL GELS AND METHODS OF USING THE SAME

(75) Inventors: Nathan Stasko, Durham, NC (US);
Susanne Bauman, Durham, NC (US);
Pranav R. Joshi, Karnataka (IN)

(73) Assignee: Novan, Inc., Durham, NC (US)

( * ) Notice: Subject to any disclaimer, the term of this patent is extended or adjusted under 35 U.S.C. 154(b) by 379 days.

(21) Appl. No.: 13/256,928

(22) PCT Filed: Aug. 20, 2010

(86) PCT No.: PCT/US2010/046173
§ 371 (c)(1),
(2), (4) Date: Oct. 4, 2011

(87) PCT Pub. No.: WO2011/022652
PCT Pub. Date: Feb. 24, 2011

(65) Prior Publication Data
US 2012/0134951 A1    May 31, 2012

Related U.S. Application Data

(60) Provisional application No. 61/235,933, filed on Aug. 21, 2009.

(51) Int. Cl.
| | | |
|---|---|---|
| A61K 9/14 | (2006.01) |
| A61K 31/655 | (2006.01) |
| A61K 9/00 | (2006.01) |
| A61K 9/06 | (2006.01) |
| A61K 33/00 | (2006.01) |
| A61K 47/24 | (2006.01) |
| A61K 47/48 | (2006.01) |

(52) U.S. Cl.
CPC ........... *A61K 31/655* (2013.01); *A61K 9/0014* (2013.01); *A61K 9/06* (2013.01); *A61K 33/00* (2013.01); *A61K 47/24* (2013.01); *A61K 47/48192* (2013.01); *A61K 47/48784* (2013.01)

(58) Field of Classification Search
CPC ........... A61K 8/72; A61K 8/89; A61K 8/891; A61K 8/73; A61K 8/732; A61K 9/0012; A61K 9/0014
USPC ................... 424/401, 402, 77.2, 484–486
See application file for complete search history.

(56) References Cited

U.S. PATENT DOCUMENTS

| | | |
|---|---|---|
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,600,001 A | 7/1986 | Gilman |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 4,985,023 A | 1/1991 | Blank et al. |
| 4,990,338 A | 2/1991 | Blank et al. |
| 5,035,892 A | 7/1991 | Blank et al. |
| 5,045,322 A | 9/1991 | Blank et al. |
| 5,061,487 A | 10/1991 | Blank et al. |
| 5,079,004 A | 1/1992 | Blank et al. |
| 5,380,758 A | 1/1995 | Stamler et al. |
| 5,405,919 A | 4/1995 | Keefer et al. |
| 5,418,301 A | 5/1995 | Hult et al. |
| 5,428,070 A | 6/1995 | Cooke et al. |
| 5,504,117 A | 4/1996 | Gorfine |
| 5,519,020 A | 5/1996 | Smith et al. |
| 5,525,357 A | 6/1996 | Keefer et al. |
| 5,574,068 A | 11/1996 | Stamler et al. |
| 5,593,876 A | 1/1997 | Stamler et al. |
| 5,599,984 A | 2/1997 | Bianchi et al. |
| 5,629,322 A | 5/1997 | Guthikonda et al. |
| 5,632,981 A | 5/1997 | Saavedra et al. |
| 5,650,442 A | 7/1997 | Mitchell et al. |
| 5,650,447 A | 7/1997 | Keefer et al. |
| 5,665,077 A | 9/1997 | Rosen et al. |
| 5,676,963 A | 10/1997 | Keefer et al. |
| 5,691,423 A | 11/1997 | Smith et al. |
| 5,693,676 A | 12/1997 | Gorfine |
| 5,700,830 A | 12/1997 | Korthuis et al. |
| 5,718,892 A | 2/1998 | Keefer et al. |
| 5,726,156 A | 3/1998 | Girten et al. |
| 5,750,573 A | 5/1998 | Bianchi et al. |
| 5,753,684 A | 5/1998 | Bianchi et al. |
| 5,760,001 A | 6/1998 | Girten et al. |

(Continued)

FOREIGN PATENT DOCUMENTS

| | | |
|---|---|---|
| CN | 1387542 | 12/2002 |
| CN | 1612804 | 5/2005 |
| CN | 1819848 | 8/2006 |
| CN | 101189032 | 5/2008 |
| CN | 101242815 | 8/2008 |
| CN | 101287505 | 10/2008 |
| EP | 0 805 678 B1 | 10/2003 |

(Continued)

OTHER PUBLICATIONS

Octanol-Water Partition Coefficients of Simple Organic Compounds, James Sangster, 1988.*

Notification of Transmittal of the International Search Report and the Written Opinion of the International Searching Authority, or the Declaration corresponding to PCT/US2012/45384 mailed Nov. 5, 2012.

Barraud, N., et al., "Involvement of Nitric Oxide in Biofilm Dispersal of Pseudomonas aeruginosa," *Journal of Bacteriology*, 2006, vol. 188(21), pp. 7344-7353.

(Continued)

*Primary Examiner* — Micah-Paul Young
(74) *Attorney, Agent, or Firm* — Myers Bigel, P.A.

(57) ABSTRACT

Provided according to some embodiments of the invention are topical gels that may release nitric oxide. Also provided are methods of using such topical gels in the treatment of wounds and other skin ailments. The topical gels comprise diazeniutndiolate-functionalized polysiloxane macromolecules.

33 Claims, 12 Drawing Sheets